(12) United States Patent
Acosta et al.

(10) Patent No.: US 6,254,826 B1
(45) Date of Patent: Jul. 3, 2001

(54) ASSAY WORK STATION

(75) Inventors: Galo F. Acosta, San Diego, CA (US); Jeffrey D. Bransky, Clarendon Hills, IL (US); Robert Case; Gregory J. Foster, both of Chicago, IL (US); Kristi K. Myers; Thomas M. Shimei, both of San Diego, CA (US); Andrew J. Woodhead, Raglan (GB)

(73) Assignee: Gen-Probe Incorporated, San Diego, CA (US)

( * ) Notice: Subject to any disclaimer, the term of this patent is extended or adjusted under 35 U.S.C. 154(b) by 0 days.

(21) Appl. No.: 09/191,343

(22) Filed: Nov. 13, 1998

Related U.S. Application Data

(60) Provisional application No. 60/065,798, filed on Nov. 14, 1997.

(51) Int. Cl.[7] .................................................... G01N 35/00
(52) U.S. Cl. .............................. 422/65; 422/63; 422/67; 422/81; 422/100; 422/104; 436/43; 436/47; 436/49; 436/54; 436/174; 436/180; 73/864.01; 73/864.11; 73/864.24; 73/864.25
(58) Field of Search ................................ 422/63, 65, 67, 422/81, 100, 104; 436/43, 47, 49, 54, 174, 180; 73/864.01, 864.11, 864.24, 864.25

(56) References Cited

U.S. PATENT DOCUMENTS

| | | |
|---|---|---|
| D. 248,045 | 5/1978 | Bassett et al. . |
| D. 250,348 | 11/1978 | Frangiosa et al. . |

(List continued on next page.)

FOREIGN PATENT DOCUMENTS

| | | |
|---|---|---|
| 3342504 A1 | 5/1985 | (DE) . |
| 0 136 126 | 4/1985 | (EP) . |
| 0210014 | 1/1987 | (EP) . |
| 0 317 286 A2 | 5/1989 | (EP) . |
| 0 796 658 A20 | 9/1997 | (EP) . |
| 0796658 | 9/1997 | (EP) . |
| WO 91/07662 | 5/1991 | (WO) . |
| 9715809 | 5/1997 | (WO) . |

OTHER PUBLICATIONS

Gitter et al., "Cytofluorometric Isolation of 1937, An Ia Antigen–Bearing Variant of the Ia–Negative Human Monocytic Cell Line U937", J. of Immunology, vol. 134, No. 1, Jan. 1985, pp. 280–283, The American Assoc. of Immunologists.

(List continued on next page.)

Primary Examiner—Jill Warden
Assistant Examiner—Kathryn Bex
(74) Attorney, Agent, or Firm—Rothwell, Figg, Ernst & Manbeck, P.C.; Charles B. Cappellari

(57) ABSTRACT

A work station for simultaneously performing multiple assays includes a base structure, a receptacle rack assembly received within a receptacle rack well formed in the base structure, a pipette tip rack assembly received within a pipette tip rack well formed in the base structure, a multiple conduit substance transfer device, and substance transfer device positioning structure. The receptacle rack assembly holds a plurality of receptacles in which a plurality of individual assays are performed, and the pipette tip rack assembly holds a plurality of contamination limiting pipette tips. The substance transfer device is capable of simultaneously dispensing substances into two or more receptacles or simultaneously removing substances from two or more receptacles. Alternatively, the substance transfer device is capable of simultaneously dispensing substances into two or more receptacles, and, at about the same time, simultaneously removing substances from two or more receptacles. The positioning structure permits the substance transfer device to be positioned with respect to the receptacle rack assembly or the pipette tip rack assembly.

25 Claims, 13 Drawing Sheets

U.S. PATENT DOCUMENTS

| | | |
|---|---|---|
| 3,807,235 | 4/1974 | Lefkovits et al. . |
| 3,938,958 | 2/1976 | Lanier et al. . |
| 3,982,438 | 9/1976 | Byrd . |
| 4,000,976 * | 1/1977 | Kramer et al. .......................... 141/98 |
| 4,058,370 | 11/1977 | Suovaniemi . |
| 4,158,035 | 6/1979 | Haase et al. . |
| 4,265,855 | 5/1981 | Mandle et al. . |
| 4,345,843 | 8/1982 | Berglund et al. . |
| 4,383,041 | 5/1983 | Kutsusawa et al. . |
| 4,459,864 | 7/1984 | Cirincione . |
| 4,478,094 | 10/1984 | Salomaa et al. . |
| 4,498,510 | 2/1985 | Minshew, Jr. et al. . |
| 4,554,839 | 11/1985 | Hewett et al. . |
| 4,599,315 | 7/1986 | Terasaki et al. . |
| 4,621,667 | 11/1986 | Eberle . |
| 4,681,742 | 7/1987 | Johnson et al. . |
| 4,803,050 * | 2/1989 | Mack ..................................... 422/65 |
| 4,824,642 | 4/1989 | Lyman et al. . |
| 4,895,650 | 1/1990 | Wang . |
| 4,925,629 | 5/1990 | Schramm . |
| 4,988,618 | 1/1991 | Li et al. . |
| 5,021,217 | 6/1991 | Oshikubo . |
| 5,092,184 | 3/1992 | Goodell et al. . |
| 5,104,808 * | 4/1992 | Laska et al. ........................... 436/48 |
| 5,139,744 * | 8/1992 | Kowalski ............................... 422/67 |
| 5,183,638 * | 2/1993 | Wakatake .............................. 422/64 |
| 5,186,760 * | 2/1993 | Rubenzer ........................... 134/22.18 |
| 5,334,352 | 8/1994 | Johnson . |
| 5,456,879 | 10/1995 | Suovaniemi . |
| 5,525,302 | 6/1996 | Astle . |
| 5,540,889 | 7/1996 | Gordon et al. . |
| 5,559,002 | 9/1996 | Uzan et al. . |
| 5,578,270 * | 11/1996 | Reichler et al. ....................... 422/67 |
| 5,645,723 | 7/1997 | Fujishiro et al. ............... 210/321.75 |
| 5,665,558 | 9/1997 | Frame et al. . |
| 5,665,562 | 9/1997 | Cook . |
| 5,736,105 | 4/1998 | Astle . |
| 5,897,783 | 4/1999 | Howe et al. . |
| 5,988,236 * | 11/1999 | Fawcett ............................... 141/130 |

OTHER PUBLICATIONS

Ledbetter et al., "T Cell Subsets Defined by Expression of Lyt–1,2,3 and Thy–1 Antigens—Two–Parameter Immunofluorescence and Cyotoxicity Analysis with Monoclonal Antibodies Modifies Current Views", J.Exp.Med., vol. 152, Aug. 1980, pp. 280–295, The Rockefeller University Press.

Lindquist et al., "A monoclonal antibody inhibiting leucocyte adhesion blocks induction of IL–2 production but not IL–2 receptor expression", Immunology, 1987, vol. 60, pp. 579–584.

Edwards et al., "Efficient Use of Monoclonal Antibodies for Immunofluorescence", Cytometry, vol. 10, 1989, pp. 94–97, Alan R. Liss, Inc.

Abstract 393B: Almasri et al., "Flow Cytometric Analysis of TdT Expression", Cytometry Supplement, 2:52, 1988, Soc. of Analytical Cytology 1988 Abstracts.

* cited by examiner

ASSAY WORK STATION

This application claims the benefit of provisional application No. 60/065,798 filed Nov. 14, 1997.

FIELD OF THE INVENTION

The present invention features a work station useful for simultaneously performing multiple biological assays in a manner that minimizes the potential for cross-contamination between individual assays.

BACKGROUND OF THE INVENTION

None of the references described or referred to herein are admitted to be prior art to the claimed invention.

Diagnostic assays are widely used in clinical diagnosis and health science research to detect or quantify the presence or amount of biological antigens, cell abnormalities, disease states, and disease-associated pathogens, including parasites, fungi, bacteria and viruses present in a host organism or sample. Where a diagnostic assay permits quantification, practitioners may be better able to calculate the extent of infection or disease and to determine the state of a disease over time. In general, diagnostic assays are based either on the detection of antigens (immunoassays) or nucleic acids (nucleic acid-based assays) belonging to an organism or virus of interest.

Nucleic acid-based assays generally include several steps leading to the detection or quantification of one or more target nucleic acid sequences in a sample which are specific to the organism or virus of interest. The targeted nucleic acid sequences can also be specific to an identifiable group of organisms or viruses, where the group is defined by at least one shared sequence of nucleic acid that is common to all members of the group and is specific to that group in the sample being assayed. The detection of individual and groups of organisms and viruses using nucleic acid-based methods is fully described by Kohne, U.S. Pat. No. 4,851,330, and Hogan, U.S. Pat. No. 5,541,551.

The first step in a nucleic acid-based assay is designing a probe which exhibits specificity, under stringent hybridization conditions, for a nucleic acid sequence belonging to the organism or virus of interest.

While nucleic acid-based assays can be designed to detect either deoxyribonucleic acid (DNA) or ribonucleic acid (RNA), ribosomal RNA (rRNA), or the gene encoding rRNA (rDNA), is typically the preferred nucleic acid for detection of a prokaryotic or eukaryotic organism in a sample. Ribosomal RNA target sequences are preferred because of their relative abundance in cells, and because rRNA contains regions of sequence variability that can be exploited to design probes capable of distinguishing between even closely related organisms. (Ribosomal RNA is the major structural component of the ribosome, which is the situs of protein synthesis in a cell.) Viruses, which do not contain rRNA, and cellular changes are often best detected by targeting DNA, RNA, or a messenger RNA (MRNA) sequence, which is a nucleic acid intermediate used to synthesize a protein. When the focus of a nucleic acid-based assay is the detection of a genetic abnormality, then the probes are usually designed to detect identifiable changes in the genetic code, such as the abnormal Philadelphia chormosome associated with chronic myelocytic leukemia. See, e.g., Stephenson et al., U.S. Pat. No. 4,681,840.

When performing a nucleic acid-based assay, preparation of the sample is necessary to release and stabilize target nucleic acids which may be present in the sample. Sample preparation can also serve to eliminate nuclease activity and remove or inactivate potential inhibitors of nucleic acid amplification (discussed below) or detection of the target nucleic acids. See, e.g., Ryder et al., U.S. Pat. No. 5,639,599, which discloses methods for preparing nucleic acid for amplification, including the use of complexing agents able to complex with ferric ions contributed by lysed red blood cells. The method of sample preparation can vary and will depend in part on the nature of the sample being processed (e.g., blood, urine, stool, pus or sputum). When target nucleic acids are being extracted from a white blood cell population present in a diluted or undiluted whole blood sample, a differential lysis procedure is generally followed. See, e.g., Ryder et al., European Patent Application No. 93304542.9 and European Patent Publication No. 0547267. Differential lysis procedures are well known in the art and are designed to specifically isolate nucleic acids from white blood cells, while limiting or eliminating the presence or activity of red blood cell products, such as heme, which can interfere with nucleic acid amplification or detection.

Before or after exposing the extracted nucleic acid to a probe, the target nucleic acid can be immobilized by target-capture means, either directly or indirectly, using a "capture probe" bound to a substrate, such as a magnetic bead. Examples of target-capture methodologies are described by Ranki et al., U.S. Pat. No. 4,486,539, and Stabinsky, U.S. Pat. No. 4,751,177. Target capture probes are generally short sequences of nucleic acid (i.e., oligonucleotide) capable of hybridizing, under stringent hybridization conditions, with a sequence of nucleic acid which also contains the target sequence. Magnets in close proximity to the reaction vessel are used to draw and hold the magnetic beads to the side of the vessel. Once the target nucleic acid is thus immobilized, the hybridized nucleic acid can be separated from non-hybridized nucleic acid by aspirating fluid from the reaction vessel and optionally performing one or more wash steps.

In most instances, it is desirable to amplify the target sequence using any of several nucleic acid amplification procedures which are well known in the art. Specifically, nucleic acid amplification is the enzymatic synthesis of nucleic acid amplicons (copies) which contain a sequence that is complementary to a nucleic acid sequence being amplified. Examples of nucleic acid amplification procedures practiced in the art include the polymerase chain reaction (PCR), strand displacement amplification (SDA), ligase chain reaction (LCR), and transcription-associated amplification (TAA). Nucleic acid amplification is especially beneficial when the amount of target sequence present in a sample is very low. By amplifying the target sequences and detecting the amplicon synthesized, the sensitivity of an assay can be vastly improved, since fewer target sequences are needed at the beginning of the assay to better ensure detection of nucleic acid in the sample belonging to the organism or virus of interest.

Methods of nucleic acid amplification are thoroughly described in the literature. PCR amplification, for instance, is described by Mullis et al. in U.S. Pat. Nos. 4,683,195, 4,683,202 and 4,800,159, and in *Methods in Enzymology*, 155:335–350 (1987). Examples of SDA can be found in Walker, PCR *Methods and Applications*, 3:25–30 (1993), Walker et al. in *Nucleic Acids Res.*, 20:1691–1996 (1992) and *Proc. Natl. Acad. Sci.*, 89:392–396 (1991). LCR is described in U.S. Pat. Nos. 5,427,930 and 5,686,272. And different TAA formats are provided in publications such as Burg et al. in U.S. Pat. No. 5,437,990; Kacian et al. in U.S. Pat. Nos. 5,399,491 and 5,554,516; and Gingeras et al. in International Application No. PCT/US87/01966 and International Publication No. WO 88/01302, and International Application No. PCT/US88/02108 and International Publication No. WO 88/10315.

Detection of a targeted nucleic acid sequence requires the use of a probe having a nucleotide base sequence which is substantially complementary to the targeted sequence or, alternatively, its amplicon.

Under selective assay conditions, the probe will hybridize to the targeted sequence or its amplicon in a manner permitting a practitioner to detect the presence of the targeted sequence in a sample. Effective probes are designed to prevent non-specific hybridization with any nucleic acid sequence which will interfere with detecting the presence of the targeted sequence. Probes may include a label capable of detection, where the label is, for example, a radiolabel, fluorescent dye, biotin, enzyme or chemiluminescent compound. Chemiluminescent compounds include acridinium esters which can be used in a hybridization protection assay (HPA) and then detected with a luminometer. Examples of chemiluminescent compounds and methods of labeling probes with chemiluminescent compounds can be found in Arnold et al., U.S. Pat. Nos. 4,950,613, 5,185,439 and 5,585,481; and Campbell et al., U.S. Pat. No. 4,946,958.

HPA is a detection method based on differential hydrolysis which permits specific detection of the acridinium ester-labeled probe hybridized to the target sequence or amplicon thereof. HPA is described in detail by Arnold et al. in U.S. Pat. Nos. 5,283,174 and 5,639,599. This detection format permits hybridized probe to be distinguished from non-hybridized probe in solution and includes both a hybridization step and a selection step. In the hybridization step, an excess of acridinium ester-labeled probe is added to the reaction vessel and permitted to anneal to the target sequence or its amplicon. Following the hybridization step, label associated with unhybridized probe is rendered non-chemiluminescent in the selection step by the addition of an alkaline reagent. The alkaline reagent specifically hydrolyzes only that acridinium ester label associated with unhybridized probe, leaving the acridinium ester of the probe-:target hybrid intact and detectable. Chemiluminescence from the acridinium ester of the hybridized probe can then be measured using a luminometer and signal is expressed in relative light units (RLU).

After the nucleic acid-based assay is run, and to avoid possible contamination of subsequent amplification reactions, the reaction mixture can be treated with a deactivating reagent which destroys nucleic acids and related amplification products in the reaction vessel. Such reagents can include oxidants, reductants and reactive chemicals which modify the primary chemical structure of a nucleic acid. These reagents operate by rendering nucleic acids inert towards an amplification reaction, whether the nucleic acid is RNA or DNA. Examples of such chemical agents include solutions of sodium hypochlorite (bleach), solutions of potassium permanganate, formic acid, hydrazine, dimethyl sulfate and similar compounds. More details of a deactivation protocol can be found in Dattagupta et al., U.S. Pat. No. 5,612,200.

When performed manually, the complexity and shear number of processing steps associated with a nucleic acid-based assay introduce opportunities for practitioner-error, exposure to pathogens, and cross-contamination between assays. Following a manual format, the practitioner must safely and conveniently juxtapose the test samples, reagents, waste containers, assay receptacles, pipette tips, aspirator device, dispenser device, and magnetic rack for performing target-capture, while being especially careful not to confuse racks, test samples, assay receptacles, and associated tips, or to knock over any tubes, tips, containers, or instruments. In addition, the practitioner must carefully perform aspirating and dispensing steps with hand-held, non-fixed instruments in a manner requiring precise execution to avoid undesirable contact between assay receptacles, aerosol formation, or aspiration of magnetic particles or other substrates used in a target-capture assay. As a further precaution, the magnetic field in a manually performed target-capture assay is often applied to only one side of the assay receptacle so that fluids can be aspirated through a pipette tip inserted along the opposite side of the assay receptacle. Although applying a magnetic field to only one side of the assay receptacle is a less efficient means for performing a target capture assay, it is designed to prevent magnetic particles from being unnecessarily aspirated as a result of practitioner inaccuracies.

Although the specific number and types of steps performed may vary between assays, the risks of error, pathogen exposure and cross-contamination in executing the steps involved in all nucleic acid-based assays is a constant concern and requires that practitioners attain a significant level of skill and dexterity. Moreover, the repetitive nature of the steps involved in a nucleic acid-based assay often leads to physical discomfort or injury, such as carpal tunnel syndrome, for those practitioners who perform high volumes of these types of assays on a daily basis. Particularly affected are practitioners working in health care laboratories, where the practitioner's sole or primary responsibility is to conduct diagnostic assays.

DETAILED DESCRIPTION OF THE PRESENTLY PREFERRED EMBODIMENT

Figure 1:
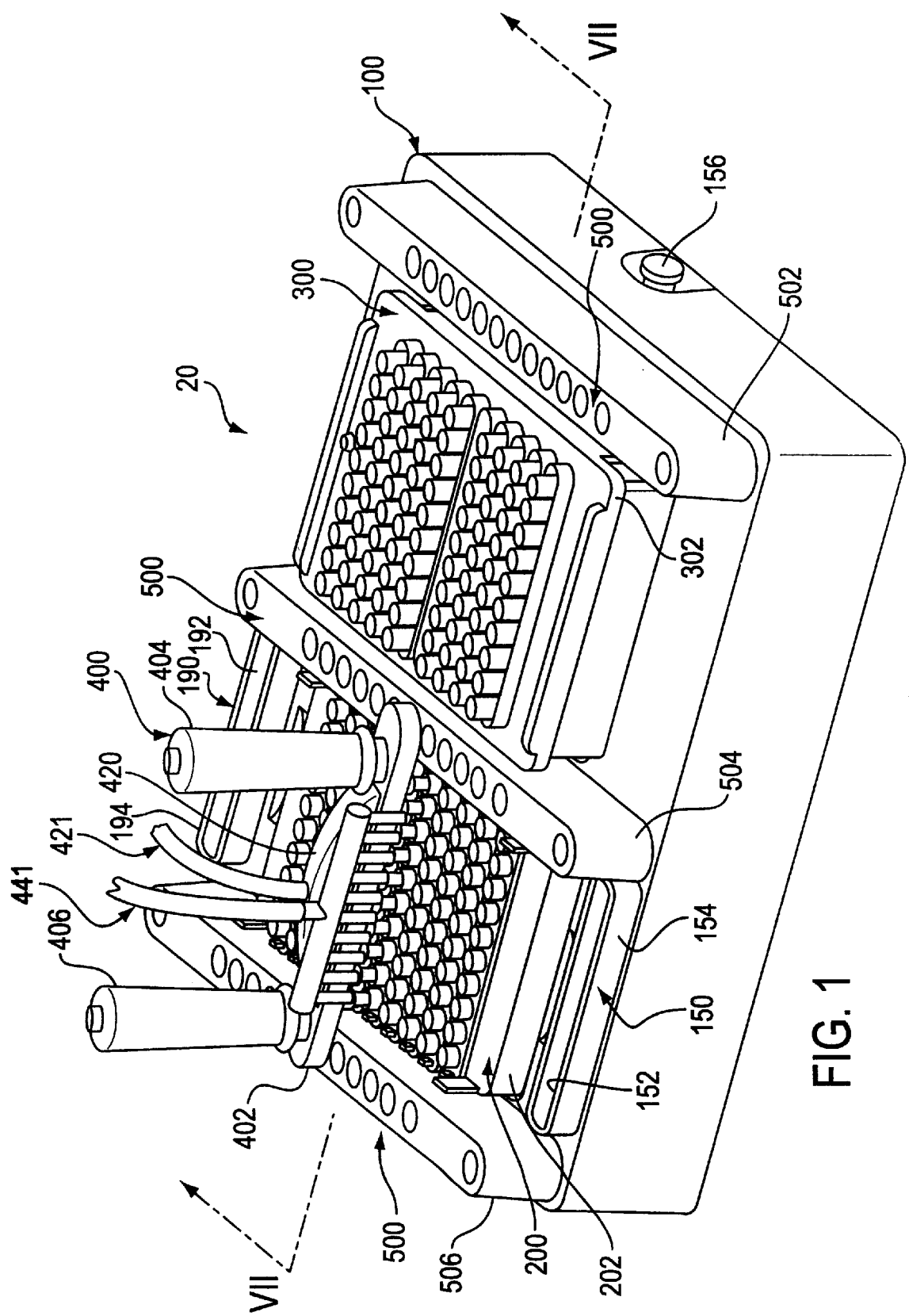
FIG. 1 is a perspective view of a work station according to the present invention.

For convenience in the following description, various directional or other spatial references are made with regard to the orientation of structure(s) shown in the drawings. It is understood, however, that such references, including, without limitation, upper, lower, top, bottom, front, back, left, right, vertical, horizontal, lateral, or longitudinal, are made for convenience only and should not necessarily be construed to be limiting on the invention described herein.

Figure 2:
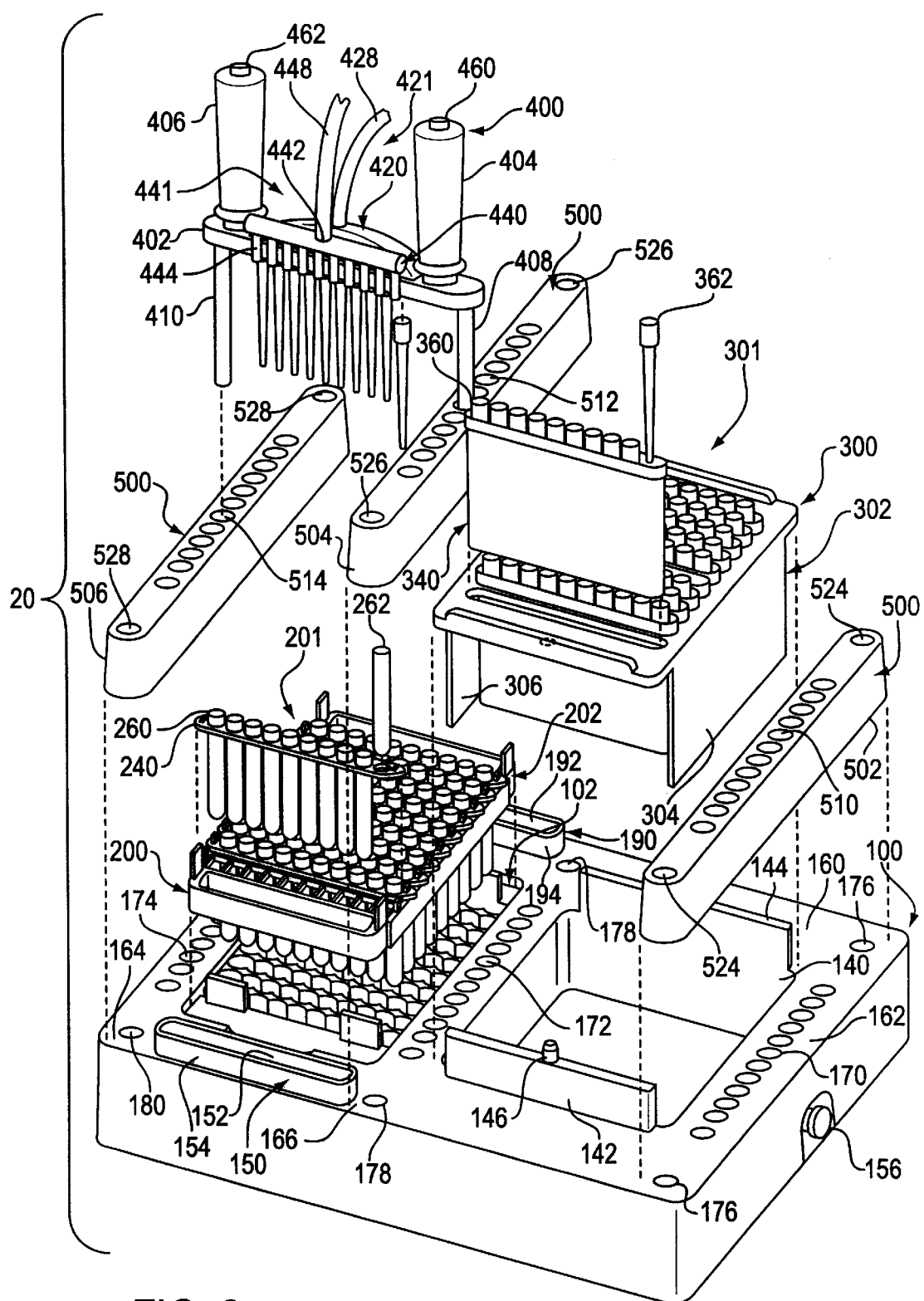
FIG. 2 is an exploded perspective view of a work station according to the present invention.
Figure 3:
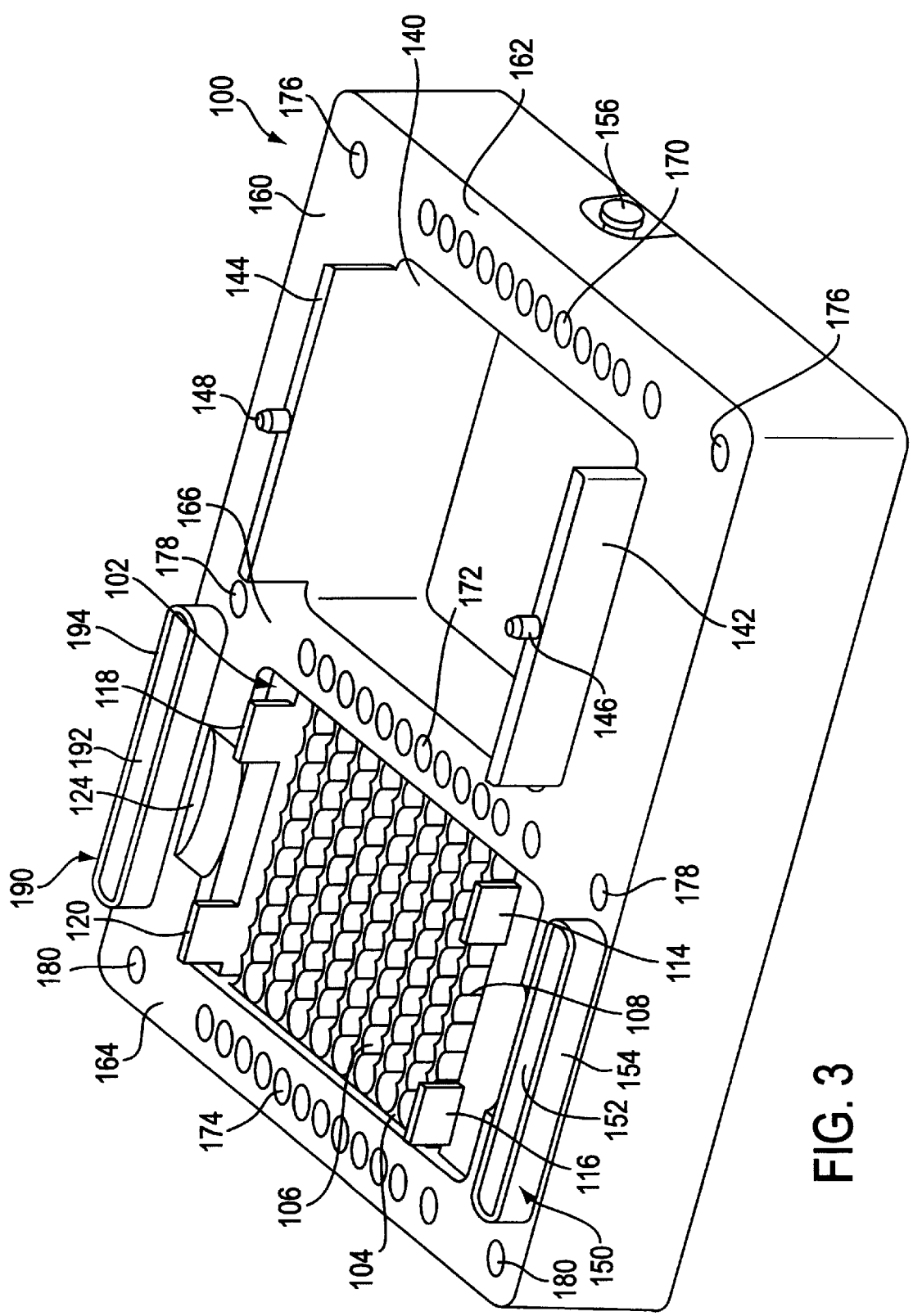
FIG. 3 is a perspective view of the base structure of a work station according to the present invention.

A work station for simultaneously performing multiple biological assays is designated generally by 20 in FIGS. 1 and 2. The work station 20 includes a base 100 preferably having a rectangular profile when viewed from the top and having a top surface 160 and integral front, back, and side walls (see FIG. 3) on which instructions or other indicia may be applied. The base 100 is preferably formed of a plastic material and more preferably of a reaction injection molded polyurethane.

Base 100 includes a first purge/prime trough 150 which comprises an elongated depression 152 formed in base 100 surrounded by a peripheral upstanding wall 154 extending around depression 152 above the top surface of base 100. In the illustrated embodiment, a second purge/prime trough 190 comprises an elongated depression 192 formed in base 100 surrounded by a peripheral upstanding wall 194 extending around depression 192 above the top surface of base 100. The second purge/prime trough 190 is optional. The purge/prime troughs 150, 190 are preferably removable from the base 100 so that any fluids in the troughs can be easily emptied and the troughs can be cleaned. In addition, the purge/prime troughs are preferably covered with a conforming stopper, or cap, when not in use to keep out environmental contaminants and to minimize evaporation. The purpose of the first and second purge/prime troughs 150, 190 will be described below.

A base knob 156 is attached at the head of a threaded pin extending into a threaded receiving aperture in the side of the base 100.

A similar knob and threaded pin are provided on the opposite side of the base 100. An optional bottom plate (not shown) extends across the bottom of base 100 and includes two upstanding tabs formed at opposite sides of the plate. The tabs have centrally-located apertures formed therein, and the plate is secured to the bottom of the base 100 by aligning the apertures formed in the tabs with the receiving apertures and inserting the threaded pins through the tab apertures and turning them into their respective threaded receiving apertures.

A receptacle holding assembly 200 is provided on one side of the base 100. The receptacle holding assembly 200 holds a plurality of receptacles 262, preferably in the form of reaction tubes, such as, for example, test tubes, as shown in the illustrated embodiment. The receptacles are preferably oriented in an array comprising a number of rows, with each receptacle being presented in an operative orientation which allows substances, such as fluids, to be dispensed into and/or removed from two or more receptacles simultaneously.

A contamination limiting element holding assembly 300 for holding a plurality of contamination limiting elements 362, e.g. pipette tips as shown in the illustrated embodiment, is provided on another side of the base 100 adjacent the receptacle holding assembly 200. The individual elements 362 are held by the assembly 300, preferably in an array comprising a number of rows of pipette tips, so as to be presented in an operative orientation so that two or more of the pipette tips may be simultaneously engaged and removed from the holding assembly 300 and subsequently be simultaneously disengaged and replaced into the assembly 300. The contamination limiting element holding assembly 300 also preferably secures each individual pipette so as to substantially prevent its contacting adjacently held pipette tips to avoid cross-contamination therebetween.

Work station 20 further includes a substance transfer device 400 which can simultaneously dispense or withdraw substances from two or more of the plurality of receptacles held in the receptacle holding assembly 200. Most preferably, substance transfer device 400 can simultaneously dispense substances into two or more receptacles of one row of receptacles while simultaneously or alternatively removing substances from two or more receptacles of another row of receptacles. The substance transfer device can also simultaneously engage and remove two or more of the pipette tips held in the contamination limiting element holding assembly 300 when the substance transfer device is moved into operative proximity with the contamination limiting element holding assembly 300.

Work station 20 also includes a substance transfer device positioning structure 500 for accurately positioning the substance transfer device 400 over either the receptacle holding assembly 200 or the contamination limiting element holding assembly 300. The positioning structure 500 facilitates accurate and repeatable positioning of the substance transfer device 400 with respect to the contamination limiting element holding assembly 300 so that two or more pipette tips of a row of pipette tips can be simultaneously engaged by the substance transfer device 400 and removed from the contamination limiting element holding assembly 300 or so that two or more pipette tips engaged by the substance transfer device 400 can be simultaneously disengaged by the substance transfer device 400 and replaced in the contamination limiting element holding assembly 300. Similarly, the positioning structure 500 facilitates accurate and repeatable positioning of the substance transfer device 400 with respect to the receptacle holding assembly 200 so that the substance transfer device 400 can simultaneously dispense substances into and/or withdraw substances from two or more receptacles of a row of receptacles held in the receptacle holding assembly 200. Additionally, the positioning structure 500 provides standby positions for storing the substance transfer device during periods of non-use.

With primary reference to FIGS. 2, 3, 6, and 7, the receptacle holding assembly 200 includes a receptacle rack well 102 formed in the base 100 and being of a generally rectangular shape. A plurality of lateral dividing walls 104 extending across the bottom of well 102 define laterally extending troughs 106. A plurality of protrusions 108, which extend vertically and are longitudinally-spaced along opposite sides of the lateral dividing walls 104, define structure for holding individual receptacles, whose ends are disposed within troughs 106, apart from one another.

Figure 7:
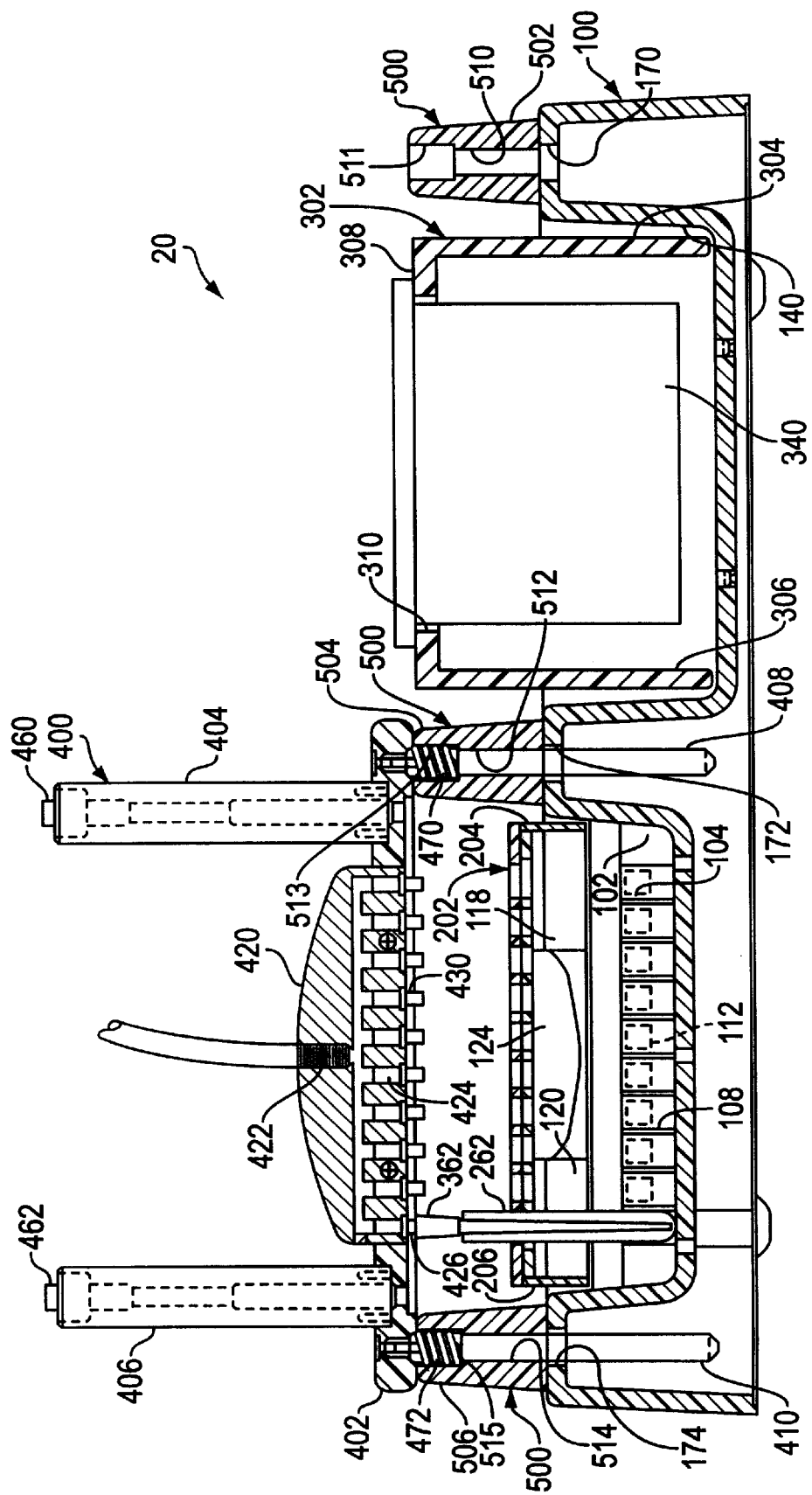
FIG. 7 is a cross-section of the work station of FIG. 1 taken along the line "VII—VII"
Figure 10:
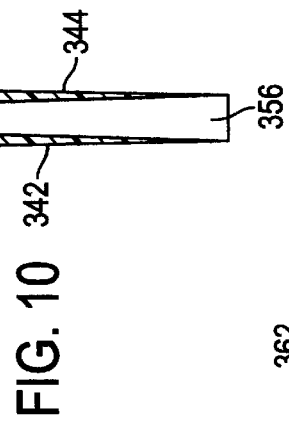
FIG. 10 is a cross-section of the cassette structure in the direction "X—X" in FIG. 8.
Figure 11:
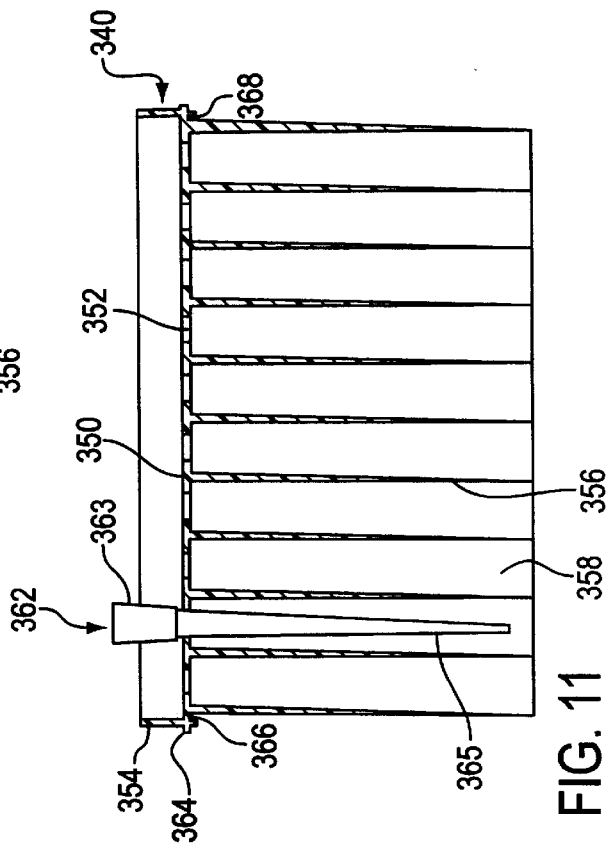
FIG. 11 is a cross-section of the cassette structure in the direction "XI—XI" in FIG. 9.
Figure 9:
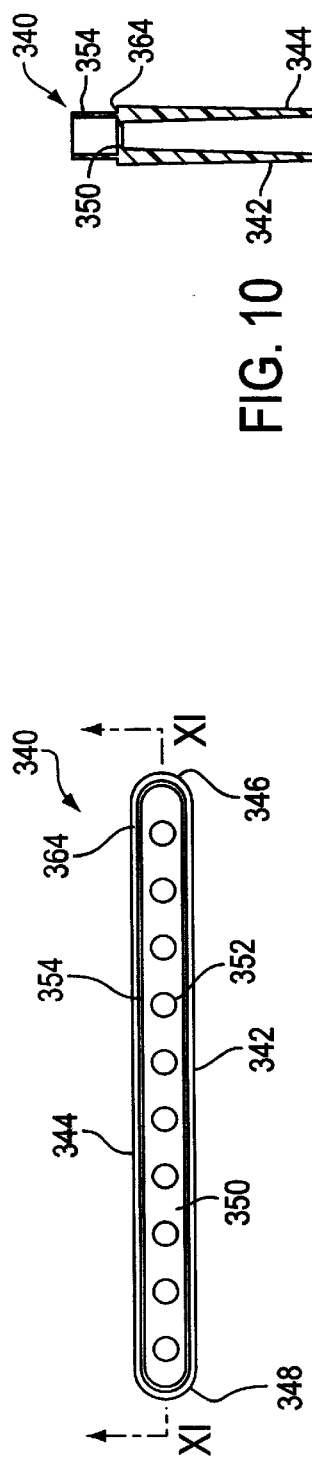
FIG. 9 is a top view of the cassette structure.
Figure 8:
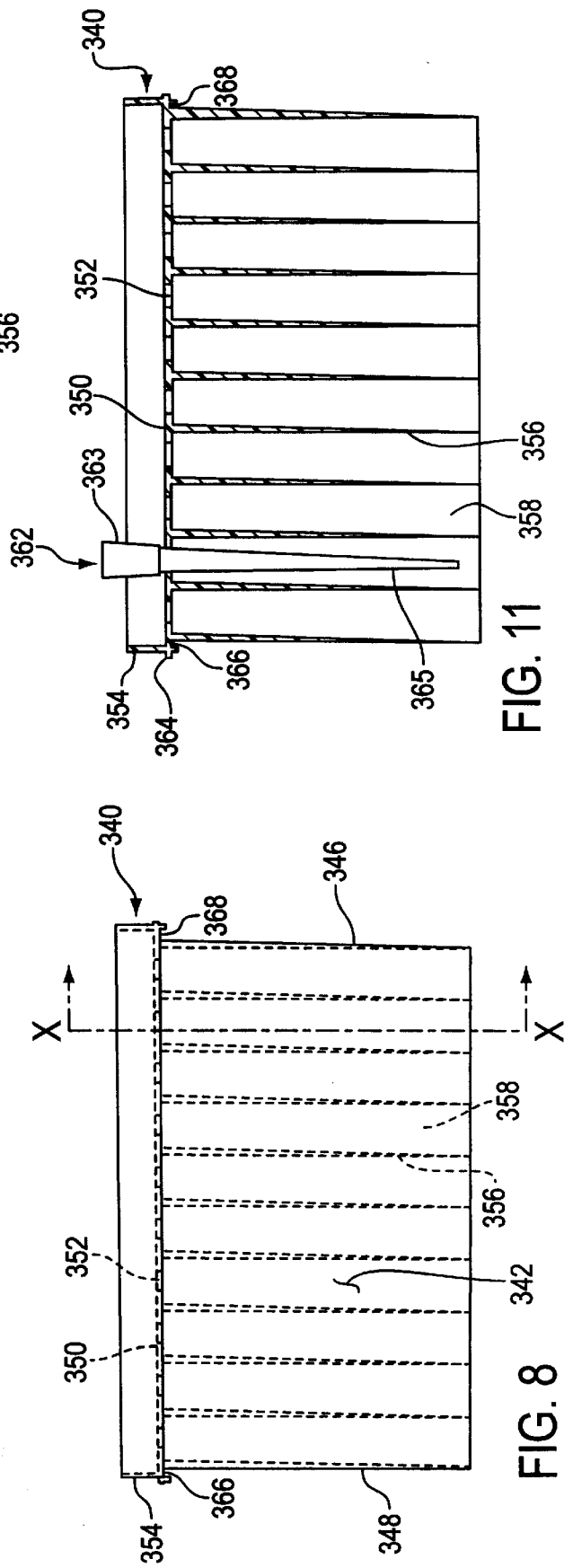
FIG. 8 is a side elevation of a cassette for holding a plurality or pipette tips.

Magnets 112, shown in phantom in FIG. 7, may be disposed within the walls 104. The magnets are preferably formed from Neodymium-Iron-Boron (NdFeB) grade n-37, have an individual size of 0.5×0.5×0.3 inches. Such magnets are provided to impart a magnetic force on solutions containing magnetic particles within receptacles disposed between the walls 104 for certain magnetic separation procedures as will be described in more detail below.

The receptacle rack well 102 preferably includes four upstanding support columns 114, 116, 118, and 120 proximate the four corners of the well 102. Support columns 114–120 may be integrally molded within the well 102 of the base 100 and preferably have a generally rectangular cross-sectional shape.

Hand wells 122 and 124 are provided on opposite ends of the receptacle rack well 102 and are disposed between columns 114, 116 and between 118, 120, respectively. The receptacle rack well 102, including the dividing walls 104, and the support columns 114–120 provide a receiving structure for accommodating a removable receptacle holding device, such as receptacle holding structure 201 described below.

Figure 5:
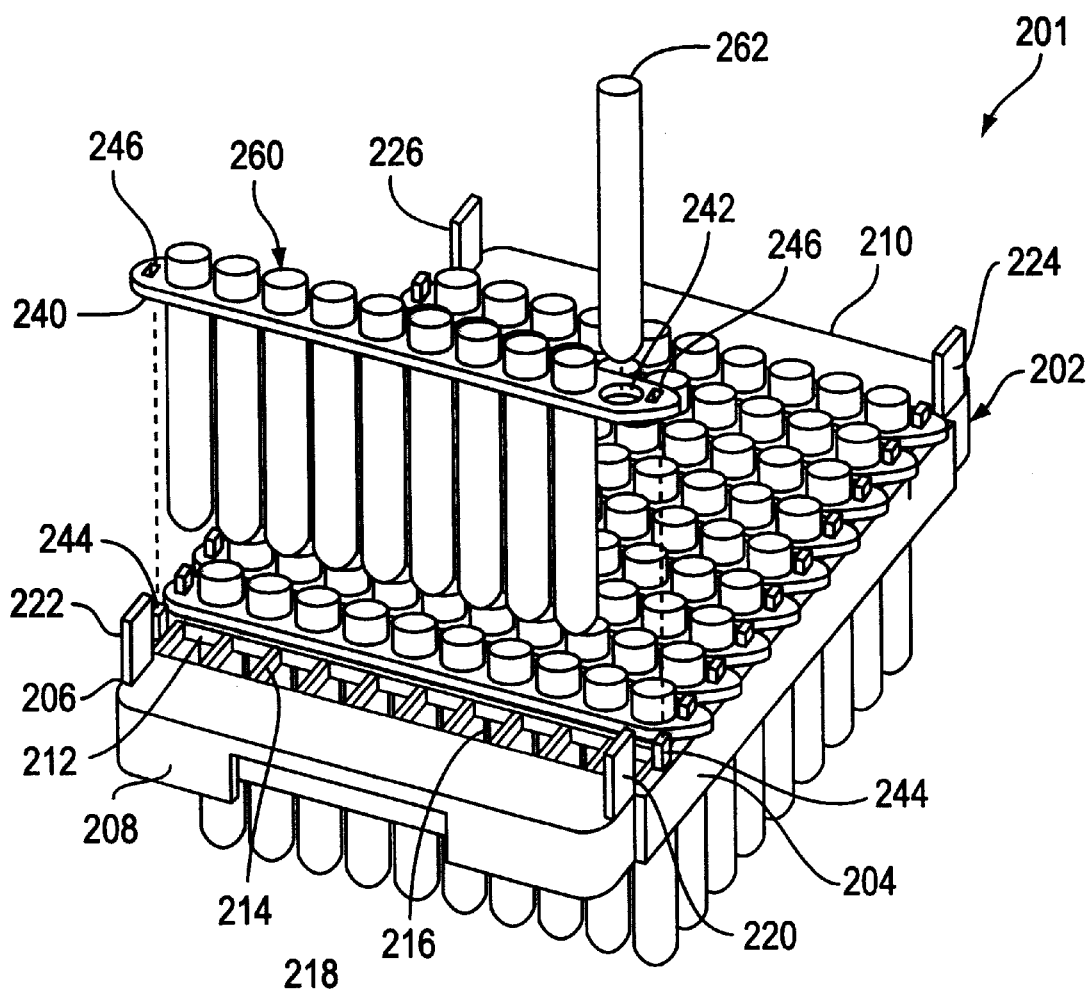
FIG. 5 is an exploded perspective view of a receptacle holding structure in the form of a removable receptacle rack for use in a work station according to the present invention.

With reference to FIGS. 2 and 5, the receptacle holding assembly 200 includes a receptacle holding structure 201 which comprises a removable receptacle rack 202. The rack 202 includes generally parallel sidewalls 204 and 206 and end wall structures 208 and 210. Four upstanding support columns 220, 222, 224, 226 preferably extend from four corners of a top portion of rack 202 for supporting thereon an optional rack cover member (not shown). A plurality of equidistantly spaced, generally parallel cross members 212 extend laterally across rack 202 from sidewall 204 to side wall 206. Also, a plurality of equidistantly spaced, generally parallel dividing members 214 extend longitudinally between adjacent cross members 212 to define a plurality of receptacle receiving box frames 216.

Preferably, nine equidistantly spaced cross members 212 are provided between end wall structures 208, 210, and preferably, nine equidistantly spaced dividing walls 214 extend between adjacent cross members 212 from side wall 204 to side wall 206. Accordingly, the cross members 212 and dividing members 214 define ten lateral rows of ten receptacle receiving box frames 216.

Receptacle rack 202 is preferably sized and configured so as to fit easily and removably within the receptacle rack well 102 of the base structure 100. Rack 202 is supported within the well 102 by means of the support columns 114, 116, 118, and 120 extending into hollow cavities defined by end wall structures 208, 210.

Finger well 218 formed in end wall structure 208 and a similar finger well (not shown) formed in end wall structure 210 cooperate with the hand wells 122 and 124 of the base structure 100 and facilitate removal and replacement of the rack 202 from and into the receptacle rack well 102.

As an alternative to the removable structure described above, a non-removable structure similar to rack 202 in construction may be fixedly secured within well 102 or a receptacle holding structure may be formed integrally within base 100.

In the preferred embodiment, the receptacle holding structure 201 further includes receptacle holding panels 240, which may be removably mounted within each row defined by cross members 212. Each panel 240 includes a plurality of apertures 242 formed therein, each aperture being aligned with one box frame 216 of receptacle rack 202 when the panel 240 is mounted to the rack 202. The size, number, and shape of the apertures formed in a panel can be varied so as to accommodate a variety of different sizes, shapes, and numbers of receptacles.

Accordingly, the receptacle rack 202 may accommodate a variety of different types and sizes of receptacles as well as various numbers of receptacles, merely by placing different receptacle holding panels 240 therein. In the preferred embodiment of the receptacle rack 202, however, ten receptacle receiving box frames 216 are provided in each row defined by cross members 212. Thus, it can be appreciated that in the preferred embodiment, each panel 240 can accommodate a maximum of ten receptacles.

Each receptacle holding panel 240 is preferably removably held within an associated row of rack 202 by means of attaching structure which may comprise tabs 244 extending upwardly from opposite ends of each row of rack 202 which may lockingly engage mating slots 246 formed in the ends of panel 240. Of course, the positions of the tabs and the mating slots could be reversed. That is, tabs could extend from panel 240 which operatively engage mating slots formed in receptacle rack 202.

Each receptacle holding panel 240 holds a plurality of individual receptacles 262, in a row 260. Preferably, receptacle rack 202 can hold ten receptacles in each of the ten rows, for a total capacity of one hundred receptacles.

It is within the contemplated scope of the present invention to provide a single removable panel, having an array of receptacle receiving apertures formed therein, which removably covers the entire upper portion of receptacle rack 202. Alternatively, a non-removable panel having an array of receptacle receiving apertures formed therein may be fixedly secured to receptacle rack 202 or integrally formed with rack 202.

While the drawings show individual, removable receptacles, i.e., test tubes, used in the work station, a modular receptacle structure in which a plurality of receptacles and a holding panel are integrally molded of a suitable material, such as plastic, is preferred. The modular structure may comprise a linear or matrix array of receptacles which are integrally formed with and connected to one another via the holding panel. It is also contemplated that some combination of removable, individual receptacles and grouped and/or nonremovable receptacles may be used as well.

When receptacle rack 202, having a plurality of receptacles 262 disposed therein, is placed into the receptacle rack well 102, the lower ends of the receptacles are received between walls 104 in the troughs 106 of well 102. The spacing between adjacent walls 104 is preferably such that the receptacles may be received therebetween with a minimum of frictional contact between the receptacles and the walls 104. In addition, the spacing between adjacent protrusions 108 corresponds to the spacing between adjacent dividing members 214 so that the protrusions 108 cooperate with the box frames 216 and apertures 242 of receptacle holding panels 240 to hold each individual receptacle in a generally upright orientation and separated from adjacent receptacles.

With primary reference to FIGS. 2, 3, 6, and 7, the contamination limiting element holding assembly 300 includes a pipette tip rack well 140 which may be integrally formed within the base 100 and which preferably defines a generally rectangular shape. The pipette tip rack well 140 provides a receiving structure for accommodating a removable contamination limiting element holding device, such as contamination limiting element holding structure 301 described below. Upwardly extending supporting end walls 142, 144 are formed on opposite sides of the well 140 and extend from the top surface 160 of the base 100.

Centrally located registration pins 146, 148 preferably extend from a top central portion of each of the end walls 142, 144, respectively.

Figure 4:
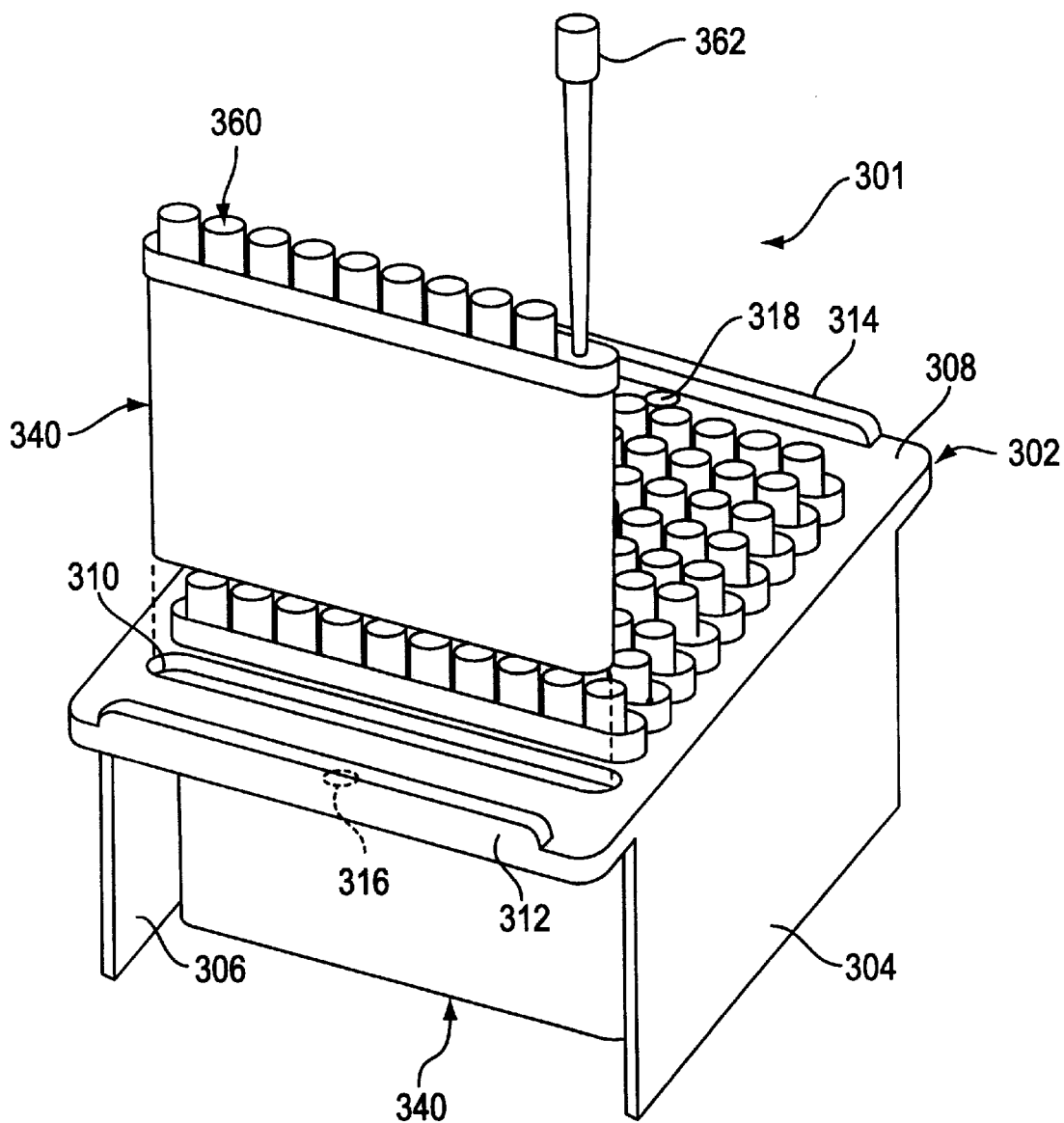
FIG. 4 is an exploded perspective view of a contamination limiting element holding structure in the form of a removable pipette tip rack and pipette tip holding cassettes for use in a work station according to the present invention.

With primary reference to FIGS. 2, 4, and 7, the contamination limiting element holding assembly 300 further includes a contamination limiting element holding structure 301, which comprises a removable pipette tip rack 302. Removable pipette tip rack 302 includes opposed, generally parallel upstanding side walls 304 and 306 with a top panel 308 extending therebetween. The removable rack 302 can be supported on its opposed side walls 304, 306 on a surface when the rack is removed from the pipette tip rack well 140. A plurality of equidistantly spaced, generally parallel slots 310 extend laterally across top panel 308. Further, registration apertures 316, 318 are centrally formed in opposite ends of the top panel 308.

Removable pipette tip rack 302 is removably disposed in an operative orientation within pipette tip rack well 140. With the removable pipette tip rack 302 installed within the pipette rack well 140, the top panel 308 rests upon and is supported by the support end walls 142, 144 and the registration apertures 316, 318 receive the registration pins 146, 148, respectively, so as to insure the proper disposition of the removable rack 302 within well 140. It can appreciated, however, that the positions of the pins and the apertures can be reversed. That is, a downwardly extending pin may be provided on the top panel 308 which would be received within a mating aperture formed in the tops of the upwardly extending support end walls 142, 144. In addition, more than one registration pin and mating aperture may be provided on each end and/or on the sides of the pipette tip rack well 140. Moreover, other registration means, such as the pipette tip rack 302 fitting snugly within pipette tip rack well 140 with little clearance, may be used to accurately position the pipette tip rack 302.

Raised edge portions 312, 314 are preferably formed along is opposite ends of the top panel 308. Edge portions 312, 314 facilitate the grasping of the rack 302 for removing the rack 302 from the well 140 and installing the rack 302 into the well 140 and further provide surfaces for supporting an optional pipette tip rack cover (not shown).

As an alternative to the removable structure described above, a non-removable structure similar in construction to rack 302 may be fixedly secured within well 140 or a pipette tip holding structure may be formed integrally within base 100.

In the preferred embodiment, the contamination limiting element holding structure 301 further includes one or more cassettes 340 for holding individual contamination limiting elements 362. Each cassette 340 is received by and removably secured within an associated one of the slots 310 formed in top panel 308 of rack 302.

As shown in FIGS. 8–11, cassette 340 comprises an elongated upright structure defined by generally parallel side walls 342, 344 connected at opposite ends thereof by end walls 346, 348 which may be arcuately-shaped, as shown. A top panel 350 extends across the top of the cassette and includes a plurality of aligned apertures 352, each for receiving an individual pipette tip. The ends of top panel 350 extend beyond end walls 346, 348 so as to define shoulders 366, 368. Each cassette 340 preferably includes ten aligned apertures 352 for holding up to ten protective pipettes 362 in a row 360, and top panel 308 preferably includes ten laterally extending slots 310. Thus, the entire pipette tip rack 302 preferably accommodates up to one hundred pipette tips 362 disposed in ten rows 360.

An upper wall 354 extends about the top panel 350 proximate the outer edge thereof. Preferably, however, top panel 350 extends peripherally beyond upper wall 354 so as to define an upwardly facing peripheral shoulder 364. A plurality of equidistantly spaced, generally parallel dividing walls 356 extend from one side wall 342 to the opposite side wall 344 for dividing the cassette 340 into a plurality of pipette tip holding compartments 358. Each of the apertures 352 opens into a one of the compartments 358. The cassette 340 shown in the drawings has no bottom wall so that the bottom end of each compartment 358 is open, but the bottom end of each compartment may, alternatively, be sealed.

A pipette tip 362 includes an upper portion 363 having a larger diameter than a lower portion 365, thereby defining an annular shoulder between the upper portion 363 and the lower portion 365 which engages the peripheral edge of aperture 352 to prevent the pipette tip 362 from falling through the cassette 340.

Each cassette 340 may include coupling structure which cooperates with associated coupling structure formed in the top panel 308 of the rack 302 for removably attaching the cassette 340 to the top panel 308. Preferably, however, each cassette is placed into a slot 310 in the rack 302 with shoulders 366, 368 of cassette 340 extending beyond the slot 310 and the cassette being held into slot 310 by its own weight.

The cassette 340 is preferably made of a suitable plastic material, and most preferably a polypropylene, and the dividing walls 356, side walls 342, 344, and end walls 342, 344, are preferably tapered so as to facilitate the forming thereof by a molding technique.

Figure 12:
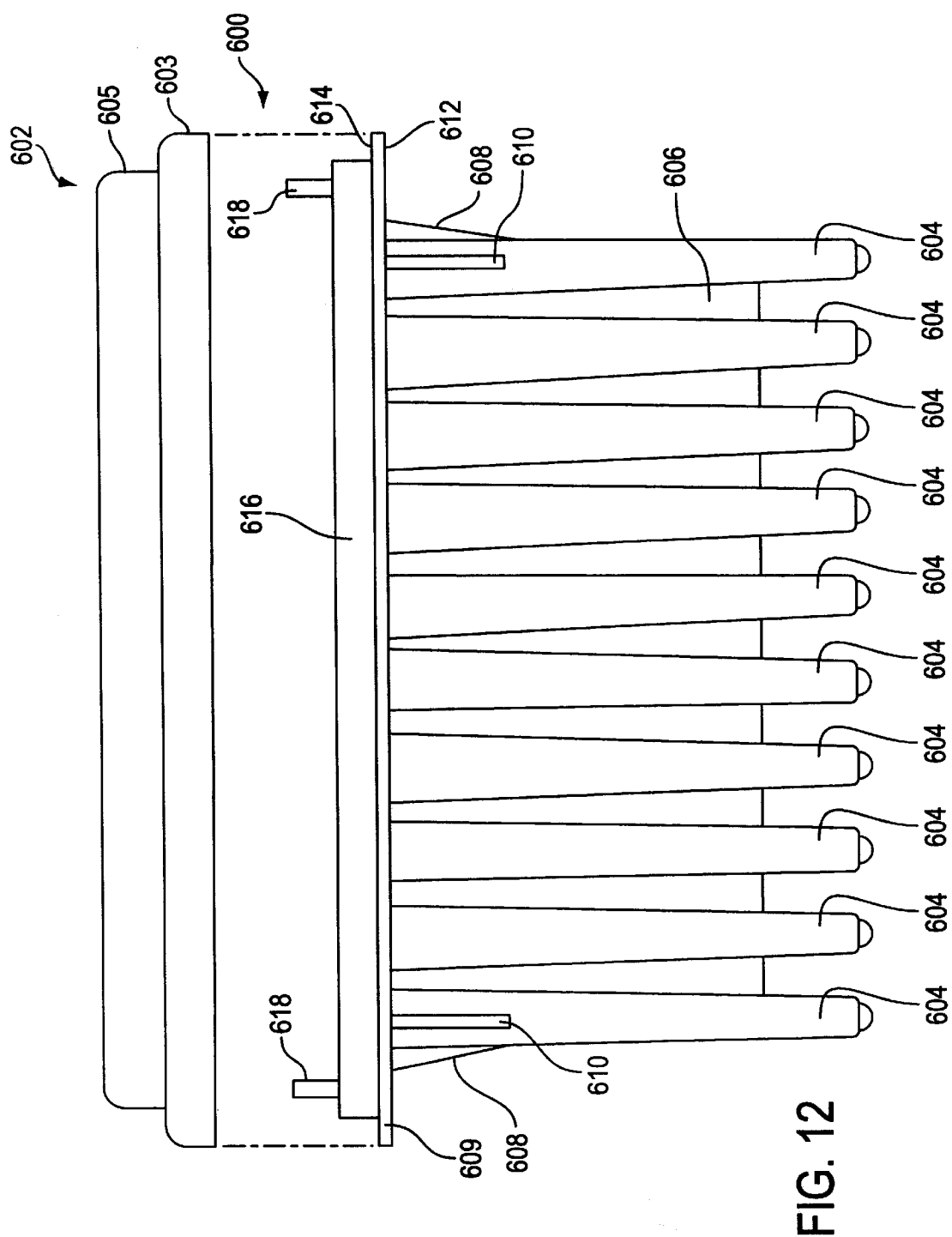
FIG. 12 is a side elevation of an alternate cassette for holding a plurality of pipettes and a cooperating cover for the cassette.
Figure 13:
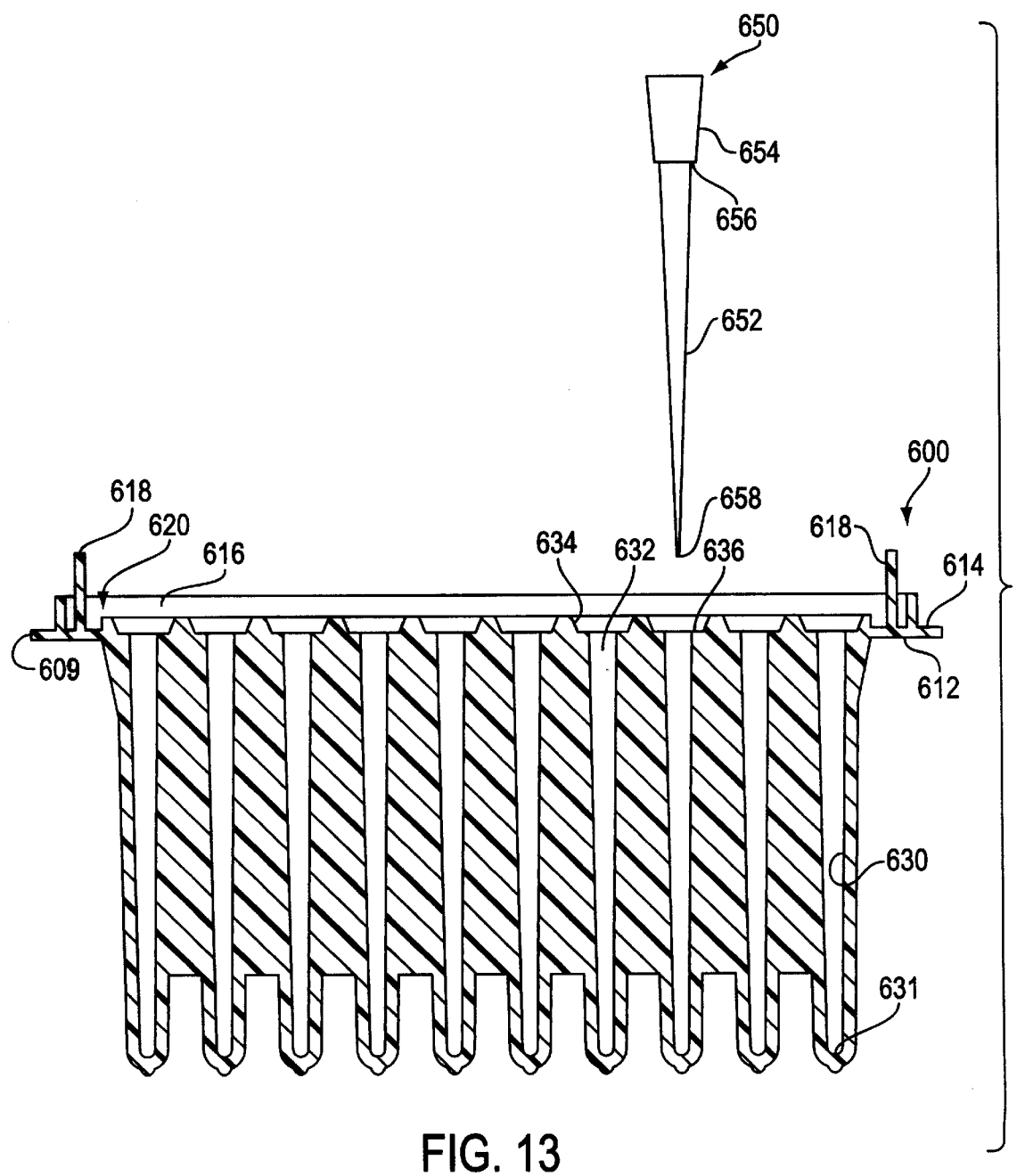
FIG. 13 is transverse cross-section of the cassette of FIG. 12.

An alternate, and preferred, cassette 600 is shown in FIGS. 12 and 13. The cassette 600 includes a plurality of pipette tip-receiving tubes 604 which are preferably slightly tapered. The tubes 604 are equidistantly spaced and are preferably oriented generally in parallel with each other. In the preferred embodiment, as shown in the figures, cassette 600 includes ten pipette tip-receiving tubes 604. Each of the individual tubes 604 is connected to one another by a connecting structure, such as thin web 606 extending between adjacent tubes 604.

A panel 609 extends across the length of cassette 602, connecting the top portions of the pipette tip-receiving tubes 604. An upwardly extending, continuous wall 616 extends from the panel 609. Panel 609 defines an upwardly facing ledge 614 and a downwardly facing ledge 612. Side ribs 608 and front and back ribs 610 (only the front ribs are visible) are formed on the side and the front and back, respectively, of the end-most tubes 604, extending down from the panel 609. Each cassette 600 fits into one of the slots 310 of the pipette tip rack 302, with the downwardly facing ledge 612 being supported on the portion of top panel 308 peripherally surrounding the slot 310. Preferably, three 90°spaced grooves (not shown) are formed at each end of slot 310 extending away from slot 310. The three ribs 608 and 610 formed on each of the end tubes 604 of the cassette 600 mate with the three grooves to stabilize the cassette 600 within slot 310. Risers 618 extend upwardly from the panel 609 and facilitate grasping of the cassette 600 to remove the cassette from the pipette tip rack 302. A cover member 602 fits over the top of the cassette 600 and is supported on the upwardly facing ledge 614. Cover member 602 includes a wide lower portion 603 which accommodates the upwardly extending wall 616 and a narrowed upper portion 605.

As shown in FIG. 13, the inner portion of each pipette tip-receiving tube 604 includes a channel 630 that is preferably tapered. A raised surface 620 extends above the panel 609 across the tops of the channels 630. Openings defining frustoconical surfaces 634 are formed in the raised surface 620. The frustoconical surfaces 634 taper inwardly toward an opening 632 of each channel 630. An annular shoulder 636 extends about the periphery of each opening 632 at the base of the frustoconical surface 634.

Each channel 630 receives an associated pipette tip 650 having a tapered lower portion 652 and an upper portion 654 of generally larger diameter than the lower portion 652. An annular shoulder 656 is defined about the base of the enlarged upper portion 654. When the pipette tip 650 is inserted into the channel 630, shoulder 656 of the pipette tip engages the shoulder 636 of the associated pipette tip-receiving tube 604, thereby limiting the extent to which the pipette tip 650 is inserted into the channel 630. The lower portion 652 of the pipette tip 650 has a length that is generally less than the length of the channel 650 below the annular shoulder 636, so that the bottom tip 658 does not contact the bottom 631 of the channel 630. The frustoconical surfaces 634 help align the pipettes 650 with the openings 632 when the pipettes are being lowered into the cassette 600.

Cassette 600 is preferably injection molded from an appropriate, non-reacting thermoplastic.

A removable drip tray (not shown) may be provided at the base of the pipette tip rack well 140 for collecting drippings from pipette tip 362 held within the cassettes 340 disposed within pipette tip rack 302, especially if cassettes having no bottom walls are used. In this way, the potential for contamination is even further limited.

Rather than the removable cassettes described above, it is within the contemplated scope of the present invention to provide a non-removable, or partially removable structure for receiving the pipette tips. For example, top surface 308 of rack 302 may have an array of pipette tip-receiving openings formed therein, and a pipette tip separating structure for preventing pipette tips from contacting one another, such as dividing walls or an egg-crate type structure, may be provided in well 140 below top surface 308, or such a separating structure may be provided as an integral component of rack 302.

With reference to FIGS. 1, 2, 7, and 12, the work station 20 further includes a substance transfer device 400, preferably a multiple conduit pipetter/aspirator device for dispensing and removing substances, typically fluids, to and from two or more receptacles simultaneously or sequentially. The substance transfer device 400 comprises an elongated horizontal frame member 402 with two upstanding handles 404, 406 projecting upwardly from opposite ends of the frame member 402 to which handles 404, 406 may be attached by suitable mechanical fasteners or the like. Handles 404, 406 may include buttons 460, 462, preferably disposed at top portions thereof. Buttons 460, 462 are coupled through handles 404, 406, respectively, to a pipette tip disengaging plate 430, disposed on the underside of frame member 402 and preferably formed from stainless steel.

Two guide rods 408, 410 extend downwardly beneath the frame member 402 from opposite ends thereof, generally below the handles 404, 406. Guide rods 408, 410 are preferably generally parallel with one another and may be attached to frame member 402 by suitable mechanical fasteners or the like. Coil springs 470, 472 are preferably disposed on guide rods 408, 410 extending below frame member 402. Springs 470, 472 are preferably installed by a push fit into counter bores 409, 411, respectively, formed in the frame 402 coaxially with the rods 408, 410. The purpose and function of the guide rods 408, 410 and the springs 470, 472 will be described in more detail below.

In the embodiment illustrated in FIGS. 1 and 2, the substance transfer device includes a substance dispensing apparatus 441 carried on the frame member 402 and constructed and arranged to dispense substances into two or more receptacles simultaneously and a substance removing apparatus 421 also carried on the frame member 402 and constructed and arranged to removed (e.g., by aspiration) substances form two or more receptacles simultaneously.

In the preferred embodiment, the substance removing apparatus 421 includes an aspirator manifold 420 operatively supported on the frame member 402 between the handles 404, 406. Aspirator manifold 420 defines a central conduit 422 which divides into a plurality, preferably ten, of branch conduits 424. Each of the branch conduits 424 has an extension portion 426 extending therefrom and through a slot 432 formed in pipette tip disengaging plate 430. A flexible tube 428, preferably formed of a plastic material, or other suitable conduit structure, extends from the central conduit 422 of the aspirator manifold 420. Tube 428 may be connected to a container (not shown) in which aspirated fluids can be stored. Alternatively, the substance removing apparatus 421 of the substance transfer device 400 may include a portable storage container carried thereby for holding aspirated substances therein.

The substance dispensing apparatus 441 includes a dispenser manifold 440, also operatively supported on frame member 402 between the handles 404, 406. Dispenser manifold 440 defines therein a central conduit 442 which divides into a plurality of branch conduits 444. A flexible tube 448, preferably formed of a plastic material, or other suitable conduit structure, extends from the central conduit 442 of the dispenser manifold 440 and may be connected to a container (not shown) which stores substances to be dispensed into receptacles. Substances are preferably supplied from a remote storage container to the substance transfer device 400 via tube 448 by a hand pump (not shown) calibrated to withdraw a predetermined amount of substance from the storage container for dispensing the predetermined amount into the receptacles through the dispenser manifold 440. Substances may be supplied from a storage container to dispenser manifold 440 by a separate metering pump mechanism (not shown) which could be operated by a hand or foot switch. A preferred dispensing pump is a 10 ml bottle top dispenser available from Wheaton under the trade name "Calibrex 520." Alternatively, a portable substance container may be provided on substance transfer device 400.

Although the substance transfer device 400 illustrated in FIGS. 1 and 2 includes both a substance removing apparatus 421 and a substance dispensing apparatus 441, the substance transfer device may include either a substance removing apparatus or a substance dispensing apparatus. Moreover, a single work station may include more than one single-function substance transfer device, e.g., a substance-removing substance transfer device and a substance-dispensing substance transfer device. Alternatively, a single substance transfer device more include more than one substance removing apparatuses and/or more than one substance dispensing apparatuses.

With primary reference to FIGS. 1, 2, 6, and 7, the work station 20, further includes a substance transfer device positioning structure 500 comprised of three elongated guide supports 502, 504, 506.

Each of the guide supports 502–506 is preferably made from Delrin and is attached to a top portion 160 of the base 100, guide support 502 being attached along a first edge 162 of the base 100, guide supports 506 being attached along an opposite edge 164, and guide support 504 being attached at top portion 166 between the receptacle rack well 102 and the pipette tip rack well 140.

Each of the guide supports 502, 504, 506 may be attached to the base 100 by any suitable means, such as for example mechanical fastener elements. Alternatively, guide supports 502–506 may be integrally molded with the base 100, may be attached to the base 100 by a suitable adhesive, or may be fixed to the base 100 by cooperating attaching structures formed on the base and the individual guides.

The guide supports 502–506 are preferably identical in construction, having a plurality of longitudinally-spaced aligned guide holes 510, 512, 514, respectively, formed therein. A plurality of longitudinally-spaced aligned guide holes 170, 172, 174 are formed in top portions 162, 166, 164, respectively, of base 100. Holes 510 align and cooperate with holes 170 when guide support 502 is attached to top portion 162, holes 512 align and cooperate with holes 172 when guide support 504 is attached to top portion 166, and holes 514 align and cooperate with holes 174 when guide support 506 is attached to top portion 164. In addition, each of the holes 510, 512, 514 is laterally aligned with an adjacent corresponding hole formed in the other guide supports.

Each of the guide supports 502, 504, 506 preferably includes fourteen guide holes 510, 512, 514, respectively. The middle twelve guide holes constitute dispensing and aspirating guide holes. Of the twelve dispensing and aspirating guide holes, the middle ten are aligned with associated rows of receptacles and pipette tips held in their respective holding structures. The first and twelfth guide holes precede the first rows of receptacles and pipette tips and follow the last rows of receptacles and pipette tips, respectively.

Each of the guide supports 502–506 also preferably includes standby holes 524, 526, 528, respectively, formed near opposite ends of the respective guide supports. The stand-by holes 524, 526, and 528 align and cooperate with associated holes 176, 178, 180, respectively, formed in top portions 162, 166, 164, respectively, of base 100. The purpose and functions of the dispensing and aspirating guide holes and the standby guide holes will be described in more detail below.

Guide supports 502 and 504, together with their respective, associated guide holes 510, 512, comprise a contamination limiting element registration structure that is constructed and arranged to register, or position, the substance transfer device with respect to the contamination limiting element holding assembly 300. Guide supports 504 and 506, together with their respective, associated guide holes 512, 514, comprise a receptacle registration structure that is constructed and arranged to register, or position, the substance transfer device 400 with respect to the receptacle holding assembly 200. The guide rods 408, 410 of the substance transfer device 400 comprise a transfer registration structure that is constructed and arranged to be selectively engaged with either the receptacle registration structure or the contamination limiting element registration structure in a manner to be described below.

Although the work station 20 preferably includes both a receptacle holding assembly 200 and a contamination limiting element holding assembly 300, so that both receptacles and pipette tips are provided in the same work space and because many assays require pipette tips in addition to receptacles, it is within the contemplation of the broader aspects of the present invention to provide a work station having only a receptacle holding assembly with a substance transfer device and substance transfer device positioning structures provided in association with the receptacle holding assembly. Such a truncated work station could still provide substantial benefits over prior art methods and apparatuses as it would allow accurate, repeatable, and simultaneous dispensing of substances into and/or withdrawing of substances from two or more receptacles disposed in the receptacle holding assembly.

Operation of the preferred embodiment of the work station of the present invention will now be described.

The substance transfer device is preferably initially stored in a standby position, with guide rods 408, 410 inserted into the standby holes 526, 528, respectively or 524, 526, respectively, located at either end of the guide supports. The exact standby position is not critical.

The receptacle holding assembly 200 is configured for performing assays by placing a receptacle rack 202 into the receptacle rack well 102 in base 100. Receptacle holding panels 240 are installed into each of one or more rows defined by the cross members 212 of the rack 202. A number of receptacles 262, corresponding to the number of assays to be performed, is inserted into the apertures 242 of the receptacle holding panels 240 until each receptacle is properly seated between the walls 104 in the receptacle rack well 102. In the preferred embodiment of the work station, integral receptacle/holding panel modules are operatively installed into the receptacle rack 202. In the case of biological assays, each receptacle will typically already contain specimen sample material, which may be derived from, for example, sputum, cervical swabs, blood, urine, puss, or stool, and each receptacle may be suitably marked to identify the specimen sample source and/or to identify the assay or assays to be performed on the specimen sample.

It is not critical that the receptacle rack 202 be first placed into the receptacle rack well 102. The receptacle holding panels 240 and/or the receptacles 262 may be placed into the rack 202 before rack 202 is placed into well 102.

The contamination limiting element holding assembly 300 is configured for performing assays by placing the pipette tip rack 302 into the pipette tip rack well 140 with each of the registration pins 146, 148 properly inserted into a mating registration aperture 316, 318, respectively. A number of contamination limiting pipette tips 362, preferably corresponding to the number of receptacles 262 installed in the receptacle rack 202, is inserted into the pipette tip rack 302.

The pipette tips 362 preferably come pre-packaged, for instance, in a cassette 340 of ten pipette tips. A cover member may be provided in the form of an elongated cap which fits over upper wall 354 and contacts the peripheral shoulder 364 of the cassette 340 to cover the pipettes held therein and prevent them from falling out of the cassette during transport and storage of the cassettes. Each cassette is also preferably wrapped in a hermetically sealed film. To set up the contamination limiting element holding assembly 300, a desired number of cassettes may be unwrapped, uncovered, and installed into the slots 310 of the pipette rack 302.

It is not critical that the pipette tip rack 302 be first placed into the pipette tip rack well 140. The cassettes 340 may be placed into the rack 302 before the rack is placed into well 140.

With the receptacle holding assembly 200 and the contamination limiting element holding assembly 300 thus set up, substances, such as reagents or buffer solutions, may be added to each of the receptacles 362 held in the receptacle holding assembly 200 by the substance transfer device 400.

The substance transfer device 400 is removed from a stand-by position and placed over the first row of receptacles, with guide rods 408, 410 aligned with the associated guide hole 512 of guide support 504 and guide hole 514 of guide support 506, respectively, to align the dispenser manifold 440 with the first row of receptacles such that each branch conduit 444 of the dispenser manifold 440 is operatively aligned is with an associated one receptacle position (i.e., with an associated receptacle receiving box frame 216 of the receptacle rack 202) in the first row. In the illustrated embodiment, ten branch conduits 444 are provided for up to ten receptacles in each row. It is contemplated, however, that less than ten receptacles may be placed in any row, and the extra branch conduits can be capped off.

In the illustrated embodiment, the aspirator manifold 420 is centered on the substance transfer device 400, i.e., arranged in series with the guide rods 408, 410, and the dispenser manifold 440 is offset from center by a distance equal to the spacing between adjacent rows 260 of receptacles, which is preferably also the spacing between adjacent rows 360 of pipette tips. Alternatively, the dispenser manifold 440 may be centered on the substance transfer device 400 and the aspirator manifold 420 may be offset, or neither manifold may be centered on the substance transfer device.

With the preferred embodiment, in which the aspirator manifold 420 is centered and the dispenser manifold 440 is offset, however, to operatively align the dispenser manifold 440 with a row of receptacles, the guide rods 408, 410 must be inserted into the guide holes 512, 514 aligned with the following row of receptacles. Thus, to align the dispenser manifold 440 with the first row of receptacles, the guide rods must be inserted into the third hole of each of the pluralities of holes 512, 514, i.e., into the second of the twelve dispensing and aspirating guide holes. In addition, to align the dispenser manifold 440 with the last row of receptacles, assuming that one-hundred receptacles 262 are held in the receptacle rack 202, the guide rods must be inserted into the second to last hole of each of the pluralities of holes 512, 514, i.e., into the twelfth dispensing and aspirating guide holes which are not aligned with the last row of receptacles. To accommodate proceeding along the rows of receptacles from either direction, a nonaligned dispensing and aspirating guide hole is provided on either end of the ten guide holes aligned with rows of receptacles and pipette tips. Thus, twelve guide holes are preferred.

With the dispenser manifold 440 properly aligned, the substance transfer device 400 is then lowered with respect to the guide supports 504, 506. As best shown in FIG. 7, guide holes 510, 512, 514 include counter-bored portions 511, 513, 515, respectively, for accommodating the springs 470, 472. As the substance transfer device 400 is lowered with respect to the guide supports 504, 506, springs 470, 472 are received within counter-bores 513, 515, respectively. The lengths of springs 470, 472 are longer than the lengths of counter-bores 513, 515, so that positive downward pressure must be applied to the substance transfer device 400 to cause the springs 470, 472 to compress within counter bores 513, 515 until the main frame member 402 of the substance transfer device 400 is properly seated on the guide supports 504, 506. The springs 470, 472 provide for a smooth, controlled descent of the substance transfer device 400 toward the guide supports 504, 506 and avoids sudden impact between substance transfer device 400 and guide supports 504, 506 should the substance transfer device be dropped.

The dispenser conduit 340 is preferably constructed so that, with the substance transfer device 400 fully lowered over a row of receptacles, no portion of the branch conduits 344 contacts an associated receptacle. With the substance transfer device thus properly positioned, substance dispensing is preferably controlled by a calibrated hand pump but can be controlled by a non-integral pump which can be actuated by a hand or foot switch.

Because, as will become more apparent shortly, the guide rods 408, 410 of the substance transfer device are repeatedly inserted into and removed from the guide holes 510, 512, 514, it is preferred that the guide holes 510, 512, 514, and especially the twelve dispensing and aspirating guide holes, be elliptical in shape so as to provide a small amount of play between the guide rods and the guide holes and thus prevent binding when the rods 408, 410 are moved in and out of the holes. Because the standby holes 524, 526, 528 are not repeatedly used, and to limit movement of the substance transfer device 400 when it is in a standby position, the standby holes 524, 526, 528 are preferably round in shape, providing a snug fit between the guide rods and the standby holes.

Next, the substance transfer device is manually lifted until the rods 408, 410 clear the holes 512, 514 associated with the first row of receptacles. The substance transfer device 400 is then manually indexed forward one row of receptacles and the rods 408, 410 are inserted into the next associated holes 512, 514 to operatively align the dispenser manifold 440 with the next row of receptacles. The substance transfer device 400 is then lowered until the main frame member 402 is seated atop the guide supports 504 and 506, and the next row of receptacles is then filled with a desired substance or substances.

These steps are repeated until the desired reaction substance or substances have been added to all of the receptacles disposed in the receptacle holding assembly 200. One or both purge/prime troughs 150, 190 can be used as a depository for excess fluids in the substance transfer device.

The substance transfer device is then replaced in a standby position. The standby holes 524, 526, 528 are preferably placed at opposite ends of the guide supports 502, 504, 506 so that the substance transfer device 400 can be placed in a standby position before the first row of pipette tips or receptacles or after the last row of pipette tips or receptacles and also to accommodate operation of the substance transfer device from either direction.

The guide holes, and especially the dispensing and aspirating guide holes, may be color-coded or marked with appropriate alpha-numeric indicia to aid in accuracy and to further avoid the chance of dispensing and aspirating errors.

At this point, depending on the requirements of the particular assay being performed, the receptacle rack 202 may be lifted out of the receptacle rack well 102 and placed on a shaker mechanism to shake the entire rack 202 to mix the contents of each of the receptacles held therein. Alternatively, or in addition, the rack may be placed in an incubator. Following a mixing and/or incubating procedure, the receptacle rack 202 may be replaced into the receptacle rack well 102. If, following the addition of magnetic particles use to capture target materials (i.e, nucleic acids), a magnetic separation procedure is to be performed in the assay, and magnets are provided in the walls 104 of the receptacle rack well 102, the rack would be allowed to set in the receptacle rack well 102 undisturbed for an appropriate period of time with the receptacles and the fluids contained therein exposed to the magnetic field, as required by the magnetic separation procedure.

Following appropriate assay steps, the next assay step may require the removal of some or all of the liquid contents, e.g., supernatant, of each of the receptacles by aspiration. To begin the aspiration sequence, the substance transfer device 400 is removed from the standby position and is placed over the contamination limiting element holding assembly 300 with the guide rods 408 and 410 inserted into the appropriate guide hole 510 of guide support 502 and guide hole 512 of guide support 504, respectively, to operatively align the aspirator manifold 420 with a first row of contamination limiting pipette tips 362 held in the contamination limiting element holding assembly 300, such that each of the branch conduits 424 of the aspirator manifold 420 is aligned with an associated pipette tips in the row. The substance transfer device 400 is then lowered toward the guide supports 502, 504. As the substance transfer device 400 is lowered with respect to the guide supports 502, 504, springs 470, 472 are received within counter-bores 511, 513, respectively. The lengths of springs 470, 472 are longer than the lengths of counter-bores 511, 513, so that positive downward pressure must be applied to the substance transfer device 400 to cause the springs 470, 472 to compress within counter bores 511, 513 until the main frame member 402 of the substance transfer device 400 is properly seated on the guide supports 502, 504. The springs 470, 472 provide for a smooth, controlled descent of the substance transfer device 400 toward the guide supports 504, 506 and avoids sudden impact between substance transfer device 400 and guide supports 502, 504 should the substance transfer device be dropped.

At this point, the extension portion 426 of each of the branch conduits 424 engages an associated one of the pipette tips in the first row of pipette tips. Preferably, each branch conduit engages an associated pipette tips by the extension portion 426 thereof extending into the upper opening of the pipette tips element so as to frictionally engage the pipette tips when the main member 402 of the substance transfer device 400 is seated on the guide supports 502 and 504.

When the substance transfer device is lifted off the guide supports 502, 504, each of the pipette tips 362 in the first row, held onto an associated extension portion 426 of the aspirating manifold 420 by friction, is lifted out of its holding compartment 358 of the first cassette 340.

Next, the substance transfer device 400 is positioned above the receptacle holding assembly 200 with the aspirator manifold 420 operatively aligned with the first row of receptacles held in the receptacle holding assembly 200 so that each pipette tip 362 held onto an associated extension portion 426 of the aspirator manifold 420 is aligned with an associated receptacle in the first row of receptacles.

Guide rods 408, 410 preferably extend lower than the bottom ends of the pipette tip 362 held onto the aspirator manifold 420 so that the rods 408, 410 engage the appropriate guide holes 512, 514 to properly align the substance transfer device 400 with the row of receptacles before the pipette tips held on the substance transfer device are brought into proximity with the receptacles. With the rods 408, 410 initially inserted into the appropriate guide holes 512, 514 for aligning the pipette tips held thereon with the first row of receptacles, the substance transfer device 400 is lowered, thus inserting each of the pipette tips engaged thereby into an associated receptacle until the main member 402 of the substance transfer device 400 is seated on the guide supports 502 and 506.

The contamination limiting pipette tips 362 limit potentially contaminating contact between the contents of each receptacle and the exterior surface of the extensions 426 of the aspirator manifold 420 because only the pipette tips, and not the extension 426 itself, is inserted into the receptacle. Such contamination limiting pipette tips are typically not necessary for dispensing substances into the receptacles because it is not necessary for any portion of the dispenser manifold 440 to be inserted into the receptacle to thereby expose the dispenser manifold 440 to the potentially contaminating contents thereof.

With the substance transfer device 400 seated on the guide supports 504, 506 and the pipette tips fully inserted into the receptacles, some or all of the contents of each receptacle is aspirated through an associated pipette tip. The substance transfer device is operatively communicated with a vacuum source (not shown) to provide suction for aspirating substances through the pipette tip and the aspirator manifold 420. The preferred vacuum source is a Gast oil-free laboratory vacuum pump, model DOPAO104AA, having a specified vacuum capacity to 25 in Hg, and manufactured by Gast Manufacturing of Benton Harbor, Mich. The aspirated fluid is transferred, by receptacle 428, preferably to a waste container.

Figure 14:
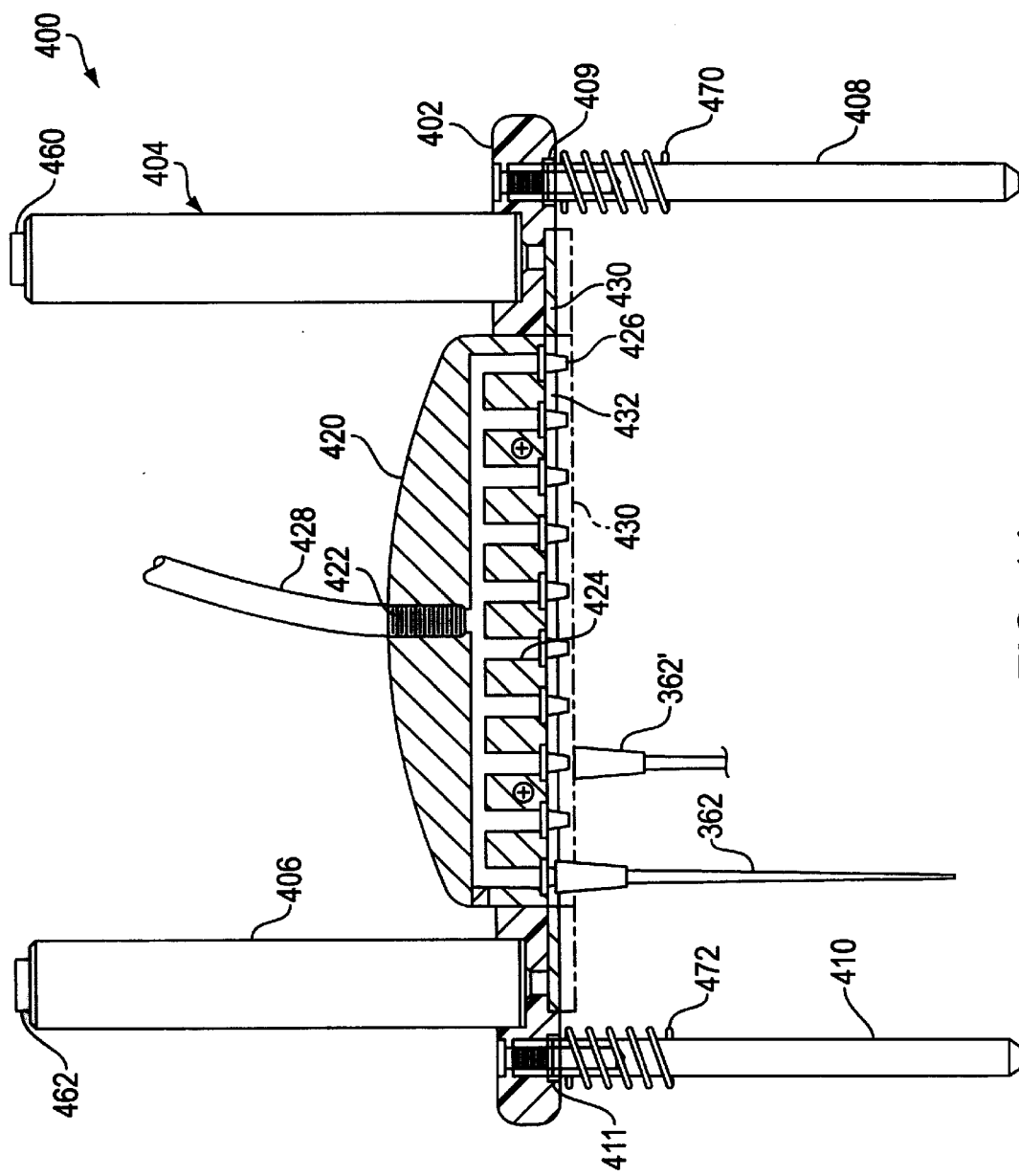
FIG. 14 is a side elevation, partially in cross-section of a substance transfer device adapted for use with the work station of the present invention.

After each of the receptacles in the first row of receptacles is aspirated, the substance transfer device 400 is manually lifted until the guide rods 408, 410 clear the associated guide holes 512, 514, and the substance transfer device 400 is then moved over the contamination limiting element holding assembly 300 so that the aspirator manifold 420 operatively aligned with the first, now empty, cassette in the pipette tip holding rack 302. Again, the lengths of the rods 408, 410 ensure that the rods enter the associated holes 510, 512, respectively, so that the aspirator manifold 420 is properly aligned with the first cassette and each pipette tip is aligned with an associated aperture 352 in the cassette before the substance transfer device is lowered. With the guide rods 408, 410 initially inserted into the guide holes 510, 512 associated with the first cassette, the substance transfer device is lowered until the frame member 402 is seated on the guide supports 502, 504 and each pipette tip is inserted through an associated aperture 352 into an associated pipette tip holding compartment 358. The pipette tips are then disengaged from the extensions 426 of the aspirator manifold 420 by pressing the buttons 460, 462 to actuate the pipette tip disengaging plate 430 by moving the plate 430 downwardly with respect to frame member 402 to the position shown in phantom in FIG. 14. Pipette tip disengaging plate 430 has formed therein an elongated slot 432 through which extensions 426 of aspirator manifold 420 extend. The width of the slot formed in plate 430 is large enough to accommodate the extension elements 426 but is smaller than the outside diameter of the top of each pipette tip 362. Thus, when pipette tip disengaging plate 430 moves downwardly, the edges of slot 432 contact the pipette tips held onto the extensions 426 and push the pipette tips off the extensions. (see FIG. 14). As an alternative to elongated slot 432, plate 430 could have formed therein a plurality of individual apertures corresponding in number and position to the extensions 426 of aspirator manifold 420, wherein the width of each aperture is large enough to accommodate an associated extension element 426 but is smaller than the outside diameter of the top of each pipette tip 362.

The substance transfer device is then lifted until the guide rods 408, 410 clear the guide holes 510, 512 and the substance transfer device is then indexed forward one row. With the guide rods 408, 410 inserted into the guide holes 510, 512 associated with the next row, or cassette, of pipette tips, the device is lowered until the frame member 402 is seated on guide supports 502, 504 and the extensions 426 of the aspirator manifold 420 engage associated pipette tips in the next row of pipette tips in the same manner as the first row of pipettes was engaged by the aspirator manifold 420.

The substance transfer device is then lifted away from the contamination limiting element holding assembly 300, with the next row of pipette tips frictionally held thereon, and moved into alignment with the next row of receptacles to be aspirated in the receptacle holding assembly 200 by inserting guide rods 408, 410 into the guide holes 512, 514 associated with the next row of receptacles. With the substance transfer device 400 properly positioned so that the aspirator manifold 420 is operatively aligned with the next row of receptacles, the substance transfer device 400 is lowered until the frame member 402 is seated on the guide supports 504, 506 and each of the pipette tips held on the aspirator manifold 420 is operatively inserted into each associated receptacle of the next row of receptacles. Thus, some or all of the contents contained in each of the receptacles in the next row can be aspirated through the pipette tips and the aspirator manifold 420.

The dispenser manifold 440 is offset from the aspirator manifold 420 so that, with the aspirator manifold 420 operatively aligned with the next row of receptacles, the dispenser manifold 440 is operatively aligned with the previous row of receptacles from which some or all of the contents has already been aspirated in the preceding aspiration sequence. Thus, assuming that the assay calls for the dispensing of additional substance(s) into the receptacles after the first aspiration, additional substance can be added to each receptacle in the preceding row of receptacles, preferably at about the same time that substance is being aspirated from each receptacle in the following row of receptacles.

The substance transfer device 400 is then lifted, moved back to the contamination limiting element holding assembly 300 to replace the pipette tips engaged therewith into their respective row, or cassette, indexed forward to engage a next row of pipette tips, and moved back to the receptacle holding assembly 200 to aspirate a next row of receptacles and optionally dispense substance into a preceding row of receptacles from which some or all of the contents thereof has been aspirated in the previous aspiration sequence.

The sequences are repeated until all of the rows of receptacles have been aspirated and, optionally, all but the last row of receptacles has been refilled by the dispenser manifold 440. After the last row of pipette tips has been replaced in its respective row, or cassette, the substance transfer device is moved back to the receptacle holding assembly 300 and positioned so that the dispenser manifold 440 is operatively aligned with the last row of receptacles, i.e., the guide rods 408, 410 are inserted into the twelfth dispensing and aspirating guide holes, which are not aligned with the last row of receptacles, and substance is then dispensed into the last row. After the last row of receptacles is filled, the substance transfer device 400 is again placed in a standby position. Alternatively, all rows may be aspirated before starting the dispense operation.

Again, depending on the requirements of the particular assay being performed, the receptacle rack 202 may be placed on a mixing device or in an incubator, and/or the receptacles may be subjected to a magnetic field within the receptacle rack well 102, or other steps may be performed.

If further aspirating and dispensing is required, the rack 202 can be replaced into the receptacle rack well 102 and the above-described steps of aspirating and dispensing can be performed with the substance transfer device until all receptacles have been aspirated and then filled.

Note that it is possible to sequentially and repeatably engage the first row of pipette tips, aspirate the first row of receptacles, replace the first row of pipette tips, engage the second row of pipette tips, aspirate a second row of receptacles, etc., so that each individual contamination limiting pipette tips is associated with and used with only one individual receptacle. After one set of receptacles has been fully processed using the work station 20, the associated set of pipette tips is discarded and fresh receptacles and fresh pipette tips are installed before commencing with the next sequence of assays.

Figure 17:
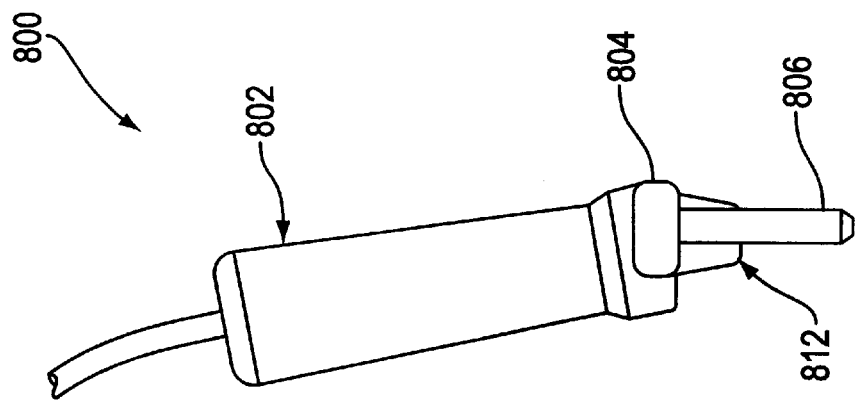
FIG. 17 is a side elevation of the substance transfer device of FIG. 16.
Figure 16:
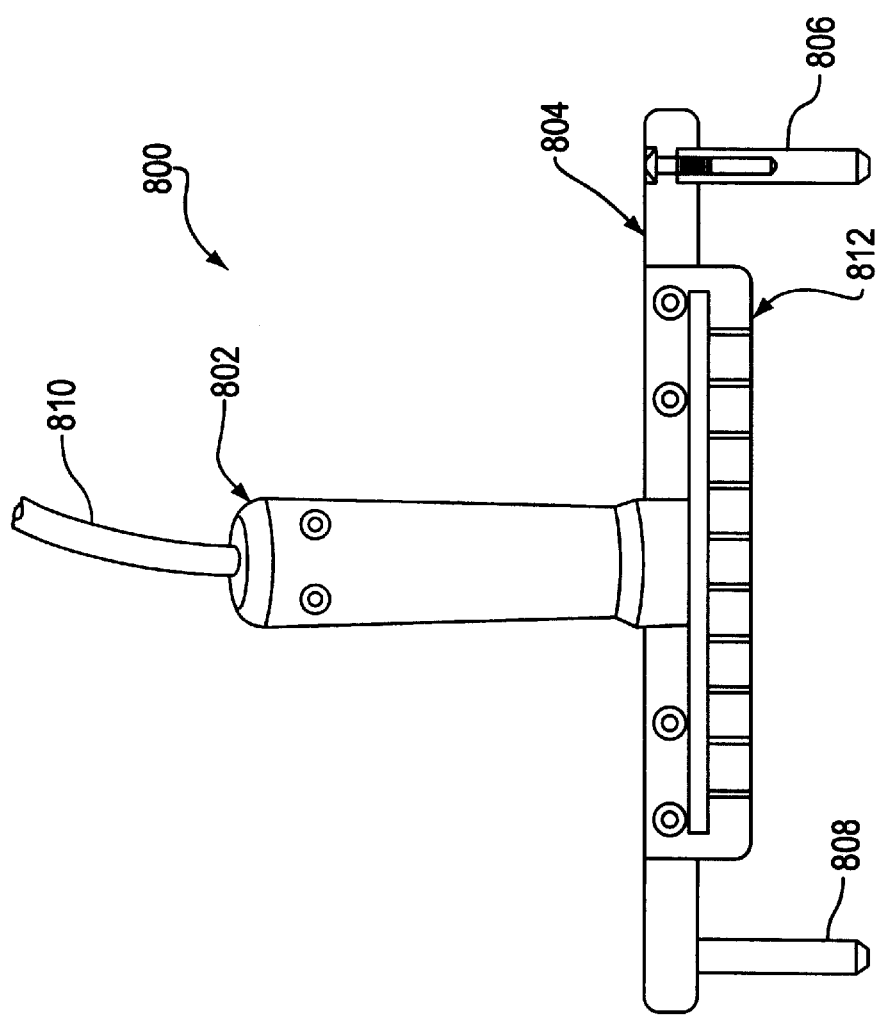
FIG. 16 is a front elevation of an alternate embodiment of a substance transfer device adapted for use with a work station according to the present invention.

An embodiment of single-function substance transfer device (i.e., a substance dispensing device or a substance removing device) is designated generally by reference number 800 in FIGS. 16 and 17. The substance transfer device 800 includes a transversely extending, elongated frame member 804 with guide rods 806 and 808 extending downwardly from opposite ends of the frame member 804. Guide rods 806 and 808 serve the same function and operate in the same manner as guide rods 408, 410 of the substance transfer device 400 described above in this specification.

A single handle 802 extends upwardly from a central portion of the frame member 804 and, as shown in FIG. 17, is preferably oriented at a slight angle (e.g., approximately 10 degrees) with respect to vertical. The substance transfer device also includes a manifold 812 defining a central conduit (not shown) and a plurality (preferably ten) of branch conduits (not shown) for engaging two or more of the receptacles and/or contamination limiting elements in a row. A flexible tube 810 extending from the handle 802 is in communication with the central conduit of the manifold 812 for transmitting substances (e.g., fluids) to or from the manifold 812.

It can be appreciated that if only a single-function substance transfer device is used with the assay work station, the guide supports need only include guide holes which align with each of the rows of receptacles, as well as stand-by holes, if desired. That is, the guide rods 806, 808 of the single function substance transfer device 800 can be aligned with the manifold 812, so that it is not necessary to dispense substance into or remove substance from a row of receptacles that is off center with respect to the guide rods 806, 808, as with the dual function device 400 described above in which the dispenser manifold 440 is off center with respect to the guide rods 408, 410.

Although substance transfer device 800 may constitute either a substance dispensing device or a substance removing device, it is preferably a substance dispensing apparatus. That is because a substance removing device would normally be used in conjunction with contamination limiting elements, and therefore the device would also preferably include a pipette disengaging plate, such as pipette disengaging plate 430 of substance transfer device 400, and the pipette disengaging plate is preferably actuated by means of buttons, such as buttons 460 and 462 of substance transfer device 400, provided in each of a pair of handles. Thus, a single handled device, such as that shown in FIGS. 16 and 17 is better suited for use as a substance dispensing device, which is typically not used in conjunction with contamination limiting elements which need to be disengaged after use.

Figure 15:
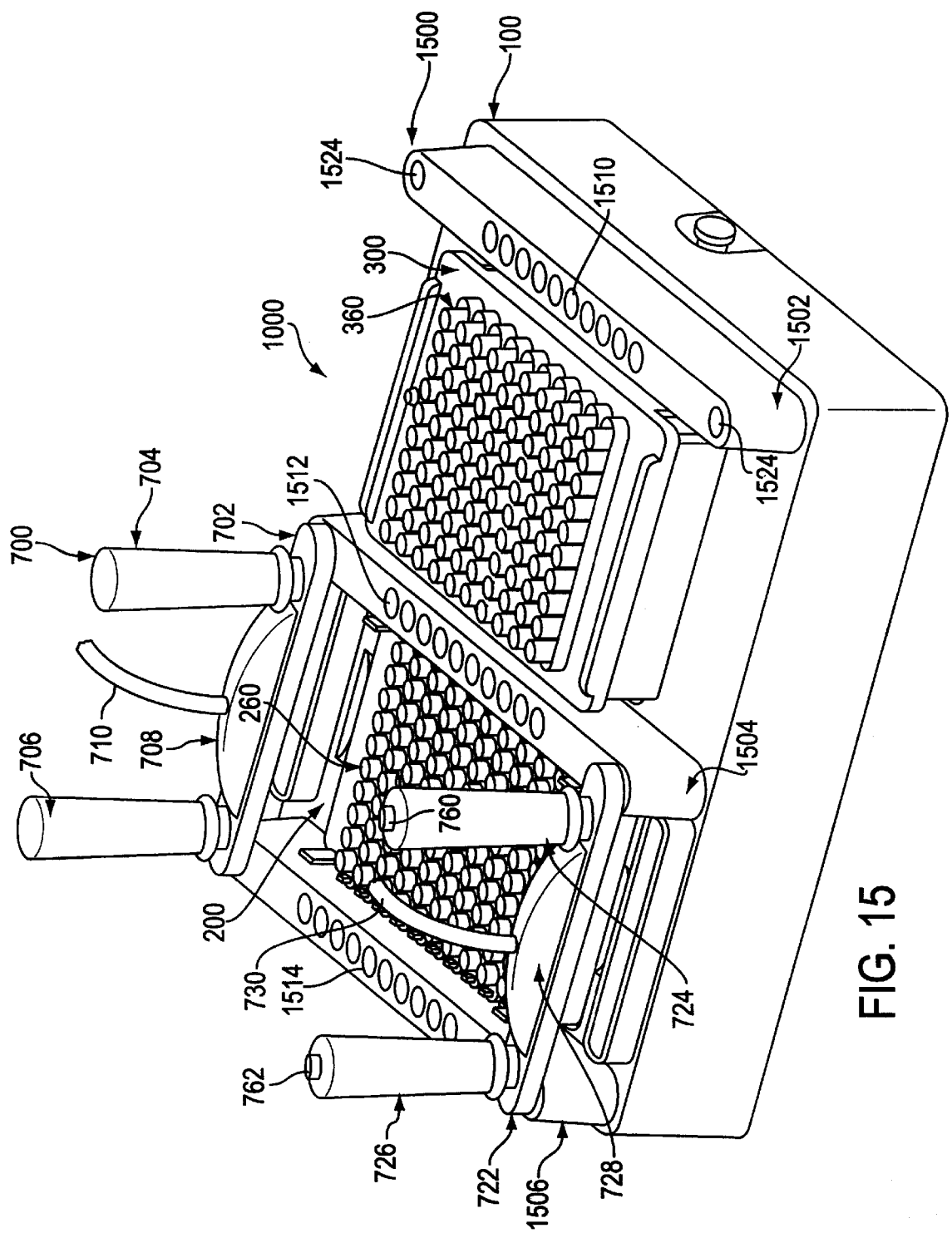
FIG. 15 is a perspective view of an alternate embodiment of a work station according to the present invention.

An alternate embodiment of a work station according to the present invention is designated generally by reference number 1000 in FIG. 15. As with the work station 20 described above, work station 1000 includes a base 100, a receptacle holding assembly 200, and a contamination limiting element holding assembly 300. Station 1000 includes a single-function, substance dispensing, substance transfer device 700 and a single-function, substance removing, substance transfer device 720. The dispensing substance transfer device 700 includes an elongated frame member 702, two upstanding handles 704, 706, and a dispensing manifold 708, with an associated conduit-tube 710. Similarly, the substance removing substance transfer device 720 includes an elongated frame member 722, two upstanding handles 724, 726, and an aspirator manifold 728, with an associated conduit-tube 730. Substance removing substance transfer device 720 also includes buttons 760, 762 for activating a pipette tip disengaging plate (not shown) similar to pipette tip removing plate 430 of substance transfer device 400 described above. Either substance transfer device 700 or 720, but especially dispensing substance transfer device 700, could be a single-handled substance transfer device, such as device 800 shown in FIGS. 16 and 17 and described above.

Station 1000 includes substance transfer guide structure 1500 including elongated guide supports 1502, 1504, 1506 having formed therein guide holes 1510, 1512, 1514, respectively. Each guide support includes stand-by holes formed at opposite ends thereof, but only stand-by holes 1524 are visible on guide support 1502, because the substance transfer devices 700, 720 are located in the stand-by positions on guide supports 1504 and 1506. Each substance transfer device 700, 720 includes guide rods (not shown) extending downwardly from its respective frame member 702, 722 to engage guide holes 1510 and 1512 or 1512 and 1514, as described above, to position the device 700, 720 with respect to either the receptacle holding assembly 200 or the contamination limiting element holding assembly 300. Because the substance transfer devices 700, 720 only include manifolds 708, 728, respectively, which are aligned with the respective guide rods of each device, the guide supports 1502, 1504, and 1506 only need guide holes 1510, 1512, and 1514 that are aligned with each of the rows 260 of receptacles and rows 360 of contamination limiting elements.

Figure 6:
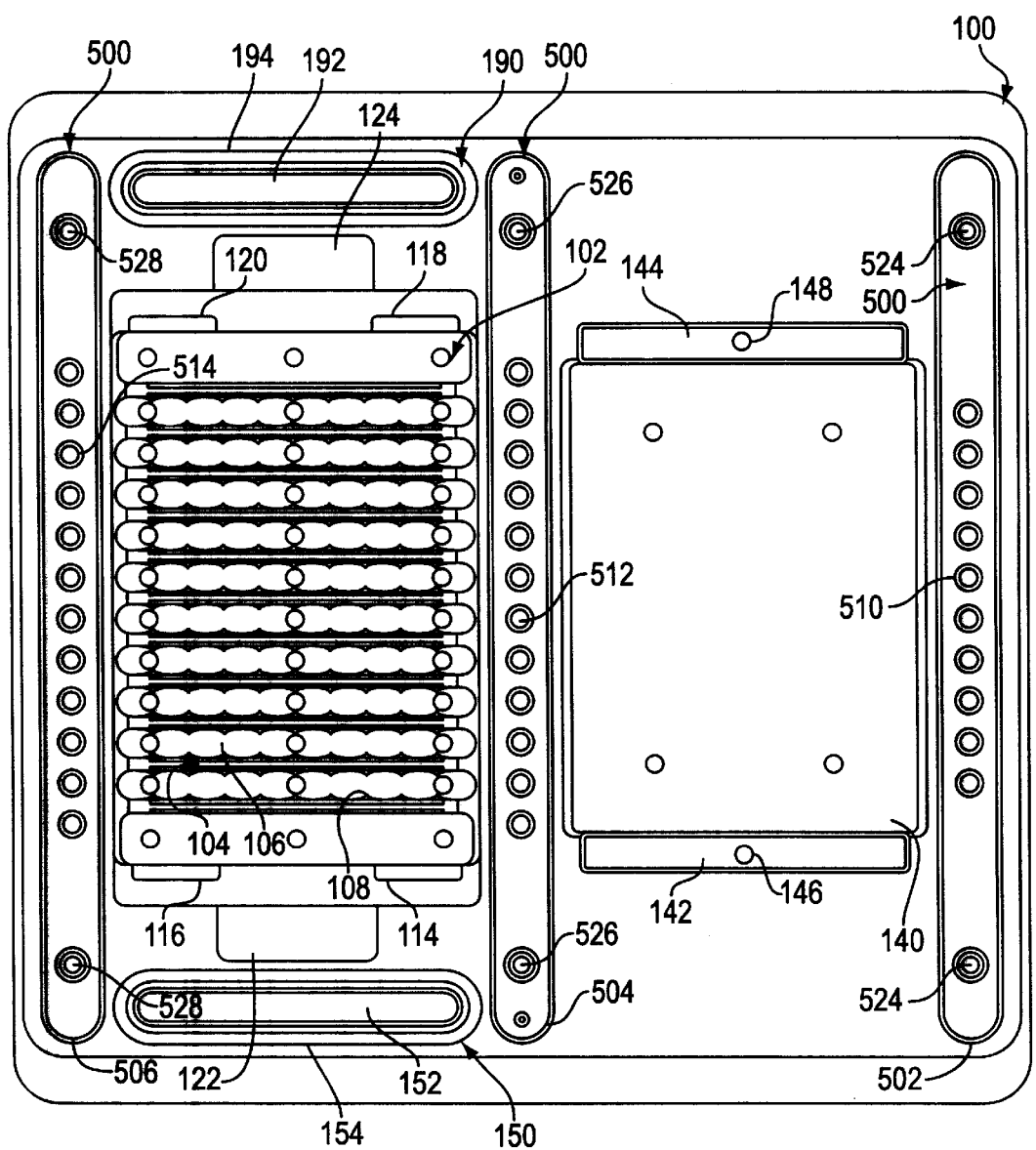
FIG. 6 is a plan view of the base structure and substance transfer device positioning structure of a work station of the present invention.

Accordingly, for the illustrated embodiment, only ten guide holes 1510, 1512, and 1514 are needed, as opposed to the twelve guide holes 510, 512, 514 needed for the embodiment of FIG. 6, which is adapted for use with the dual function substance transfer device 400, including the off center dispenser manifold 440.

It will be realized that the foregoing preferred specific embodiment of the present invention has been shown and described for the purposes of illustrating the functional and instructional principles of this invention and are subject to change without departure from such principles. Therefore, this invention includes all modifications encompassed within the spirit and scope of the following claims.

What is claimed is:

1. A work station for simultaneously performing multiple assays, said work station comprising:
   (a) a receptacle holding structure constructed and arranged to hold each of a plurality of receptacles in one of a plurality of receptacle sets, each set including at least two receptacles;
   (b) a substance transfer device constructed and arranged to operatively interact with the receptacles of at least two of the receptacle sets held in said receptacle holding structure to simultaneously dispense substance into each of the receptacles of a first receptacle set of the at least two receptacle sets and to simultaneously remove substance from each of the receptacles of a second receptacle set of the at least two receptacle sets, wherein said substance transfer device is constructed and arranged to simultaneously remove substance from each of the receptacles of the second receptacle set at about the same time that said substance transfer device is simultaneously dispensing substance into each of the receptacles of the first receptacle set; and
   (c) a substance transfer device positioning mechanism including first registration elements associated with portions of said receptacle holding structure corresponding to each of said receptacle sets and second registration elements fixed to said substance transfer device and constructed and arranged to be selectively engageable with a portion of said first registration elements to thereby position said substance transfer device with respect to any two or more of the receptacle sets held in said receptacle holding structure to allow said substance transfer device to:
     (i) simultaneously dispense substance into each of the receptacles of a first receptacle set of the two or more receptacle sets,
     (ii) simultaneously remove substance from each of the receptacles of a second receptacle set of the two or more receptacle sets, or
     (iii) simultaneously dispense substance into each of the receptacles of the first receptacle set and simultaneously remove substance from each of the receptacles of the second receptacle set at about the same time that said substance transfer device is simultaneously dispensing substance into each of the receptacles of the first receptacle set.

2. The work station of claim 1, wherein
said first registration elements comprise a pair of elongated guide supports, one of said elongated guide supports being positioned on either side of said receptacle holding structure, each of said elongated guide supports having a plurality of aligned, vertically extending guide holes formed therein, each of said guide holes of one of said pair of elongated guide supports being aligned with a corresponding guide hole of the other of said elongated guide supports,
said second registration elements comprise a pair of spaced, generally parallel guide rods extending from said substance transfer device, and
one of said guide rods of said second registration elements is constructed and arranged to be inserted into a one of said guide holes of one of said elongated guide supports of said first registration elements and the other of said guide rods of said second registration elements is constructed and arranged to be inserted into said corresponding guide hole of the other of said elongated guide supports of said first registration elements to position said substance transfer device with respect to said receptacle holding structure to allow said substance transfer device to:
   (i) simultaneously dispense substance into each of the receptacles of the first receptacle set,
   (ii) simultaneously remove substance from each of the receptacles of the second receptacle set, or
   (iii) simultaneously dispense substance into each of the receptacles of the first receptacle set and simultaneously remove substance from each of the receptacles of the second receptacle set at about the same time that said substance transfer device is simultaneously dispensing substance into each of the receptacles of the first receptacle set.

3. A work station for simultaneously performing multiple assays, said work station comprising:
(a) a receptacle holding structure constructed and arranged to hold each of a plurality of receptacles in one of a plurality of receptacle sets, each set including at least two receptacles;
(b) a substance transfer device constructed and arranged to operatively interact with the receptacles of at least two of the receptacle sets held in said receptacle holding structure to simultaneously dispense substance into each of the receptacles of a first receptacle set of the at least two receptacle sets and to simultaneously remove substance from each of the receptacles of a second receptacle set of the at least two receptacle sets, wherein said substance transfer device is constructed and arranged to simultaneously remove substance from each of the receptacles of the second receptacle set at about the same time that said substance transfer device is simultaneously dispensing substance into each of the receptacles of the first receptacle set;
(c) a contamination limiting element holding structure for removably holding a plurality of contamination limiting elements which are operatively engageable by said substance transfer device to limit contact between said substance transfer device and a potentially contaminating substance dispensed or removed by said substance transfer device, and contamination limiting element holding structure being constructed and arranged to:
   (i) receive and removably hold the plurality of contamination limiting elements in an operative orientation in which the contamination limiting elements can be operatively engaged by said substance transfer device, and
   (ii) allow said substance transfer device to simultaneously engage two or more of the plurality of contamination limiting elements and allow the two or more contamination limiting elements engaged by said substance transfer device to be removed from said contamination limiting element holding structure; and
(d) a substance transfer device positioning mechanism including the receptacle registration structure associated with portions of said receptacle holding structure corresponding to each of said receptacle sets, a transfer registration structure fixed to said substance transfer device, and a contamination limiting element registration structure associated with said contamination limiting element holding structure,
   (i) said transfer registration structure being constructed and arranged to be selectively engageable with a portion of said contamination limiting element registration structure to thereby permit said substance transfer device to be positioned with respect to said contamination limiting element holding structure to allow said substance transfer device to operatively engage the two or more contamination limiting elements, and
   (ii) said transfer registration structure being constructed and arranged to be selectively engageable with a portion of said receptacle registration structure to thereby position said substance transfer device with respect to any two or more of the receptacle sets held in said receptacle holding structure to permit said substance transfer device to:
      (1) simultaneously dispense substance into each of the receptacles of a first receptacle set of the two or more receptacle sets,
      (2) simultaneously remove substance from each of the receptacles of the second receptacle set of the two or more receptacle sets, or
      (3) simultaneously dispense substance into each of the receptacles of the first receptacle set and simultaneously remove substance from each of the receptacles of the second receptacle set at about the same time that said substance transfer device is simultaneously dispensing substance into each of the receptacles of the first receptacle set.

4. The work station of claim 3, further comprising a plurality of contamination limiting elements removably held by said contamination limiting element holding structure.

5. The work station of claim 3, further comprising a plurality of receptacles held by said receptacle holding structure.

6. The work station of claim 3, said contamination limiting element holding structure comprising one or more cassettes for holding a plurality of contamination limiting elements, each said cassette comprising:
   side walls which are spaced apart and generally parallel to one another;
   end walls which are opposed to one another and extend between said side walls at opposite ends thereof; and
   a top panel having a plurality of apertures for receiving a plurality of contamination limiting elements formed therein, each said aperture adapted receive one of the plurality of contamination limiting elements.

7. The work station of claim 6, wherein each said cassette further comprises a plurality of dividing walls which are spaced apart and extend between said side walls and, in combination with said side walls and said end walls, define a plurality of contamination limiting element compartments, wherein each said compartment is capable of housing one of the contamination limiting elements.

8. The work station of claim 7, further comprising a plurality of contamination limiting elements, each of said plurality of contamination limiting elements being housed in an associated one of said plurality of contamination limiting element compartments.

9. The work station of claim 3, said contamination limiting element holding structure comprising one or more cassettes for holding a plurality of contamination limiting elements, each said cassette comprising:
   a plurality of contamination limiting element-receiving tubes, each of said tubes having a channel formed therein for receiving a contamination limiting element and an opening for providing access to said channel;
   a connecting structure holding said tubes together as an integral unit; and
   a frustoconical surface surrounding said opening for facilitating alignment of a contamination limiting element with said opening.

10. The work station of claim 3, wherein said receptacle holding structure, said contamination limiting element holding structure, and said substance transfer device positioning structures are all operatively disposed on a base structure.

11. The work station of claim 3, wherein said receptacle holding structure comprises a receptacle rack for holding a plurality of receptacles arranged in an array.

12. The work station of claim 11, further comprising a base structure, said base structure including a receptacle rack well formed in said base structure, wherein said receptacle rack is constructed and arranged to be removably disposed within said receptacle rack well.

13. The work station of claim 12, wherein said receptacle holding structure further comprises one or more removable receptacle holding panels having a plurality of receptacle receiving apertures formed therein, said one or more removable receptacle holding panels being removably attachable to said receptacle rack for providing insert apertures by which each of the receptacles is inserted into said receptacle rack.

14. The work station of claim 3, wherein said contamination limiting element holding structure comprises a pipette tip rack for holding a plurality of pipette tips arranged in an array.

15. The work station of claim 14, wherein said pipette tip rack comprises a top panel and upstanding sidewall structures supporting said top panel, said top panel having formed therein a plurality of slots arranged generally in parallel with one another, and wherein said contamination limiting element holding structure further comprises one or more cassettes for holding a plurality of contamination limiting elements, each of said one or more cassettes being constructed and arranged to be operatively positioned in an associated one of said slots formed in said top panel.

16. The work station of claim 14, further comprising a base structure, said base structure including a pipette tip rack well formed in said base structure, said pipette tip rack being constructed and arranged to be removably disposed within said pipette tip rack well.

17. The work station of claim 3, wherein said substance transfer device comprises:
  (a) an elongated central support member;
  (b) a pair of upstanding handle members attached to and extending upwardly from said central support member proximate opposite ends thereof;
  (c) a substance dispensing apparatus operatively mounted to said central support member and including two or more conduits, said substance dispensing apparatus being constructed and arranged to simultaneously dispense substance from each of said two or more conduits of said substance dispensing apparatus into each of the two or more receptacles of the first set; and
  (d) a substance removing apparatus operatively mounted to said central support member and including two or more conduits, said substance removing apparatus being constructed and arranged to simultaneously remove substance through each of said conduits of said substance removing apparatus from each of the two or more receptacles of the second set, wherein said substance removing apparatus is constructed and arranged to remove substance from each of the two or more receptacles of the second set at about the same time said substance dispensing apparatus is dispensing substance into each of the two or more receptacles of the first set.

18. The work station of claim 17, wherein said substance dispensing apparatus comprises a dispenser manifold defining a central conduit and two or more branch conduits extending from said central conduit, said central conduit of said dispenser manifold being connected to a source of substance to be dispensed into the receptacles, and, wherein said substance removing apparatus comprises an aspirator manifold defining a central conduit and two or more branch conduits extending from said central conduit through which substances are removed from the receptacles by aspiration; said central conduit of said aspirator manifold being connected to a container for storing substances aspirated from the receptacles.

19. The work station of claim 3,
  wherein said receptacle registration structure comprises a pair of elongated guide supports, one of said elongated guide supports being positioned on either side of said receptacle holding structure, each of said elongated guide supports having a plurality of aligned, vertically extending guide holes formed therein, each of said guide holes of one of said pair of elongated guide supports being aligned with a corresponding guide hole of the other of said elongated guide supports,
  wherein said contamination limiting element registration structure comprises a pair of elongated guide supports, one of said elongated guide supports being positioned on either side of said contamination limiting element holding structure, each of said elongated guide supports having a plurality of aligned, vertically extending guide holes formed therein, each of said guide holes of one of said pair of elongated guide supports being aligned with a corresponding guide hole of the other of said elongated guide support, and
  wherein said transfer registration structure comprises a pair of spaced, generally parallel guide rods extending from said substance transfer device,
  wherein one of said guide rods of said transfer registration structure is constructed and arranged to be inserted into a one of said guide holes of one of said elongated guide supports of said contamination limiting element registration structure and the other of said guide rods of said transfer registration structure is constructed and arranged to be inserted into said corresponding aligned guide hole of the other of said elongated guide supports of said contamination limiting element registration structure to position said substance transfer device with respect to said contamination limiting element holding structure to allow said substance transfer device to operatively engage the two or more contamination limiting elements, and
  wherein one of said guide rods of said transfer registration structure is constructed and arranged to be inserted into a one of said guide holes of one of said elongated guide supports of said receptacle registration structure and the other of said guide rods of said transfer registration structure is constructed and arranged to be inserted into said corresponding guide hole of the other of said elongated guide supports of said receptacle registration structure to position said substance transfer device with respect to said receptacle holding structure to allow said substance transfer device to:
    (i) simultaneously dispense substance into each of the receptacles of the first receptacle set,
    (ii) simultaneously remove substance from each of the receptacles of the second receptacle set, or
    (iii) simultaneously dispense substance into each of the receptacles of the first receptacle set and simultaneously remove substance from each of the receptacles of the second receptacle set at about the same time that said substance transfer device is simultaneously dispensing substance into each of the receptacles of the first receptacle set.

20. The work station of claim 12, further comprising a plurality of spaced, substantially parallel dividing walls extending laterally across a bottom portion of said receptacle rack well so as to define a plurality of spaced, laterally extending, substantially parallel receptacle receiving troughs across said bottom portion of said receptacle rack well for receiving therein portions of the plurality of receptacles held in said receptacle rack.

21. The work station of claim 20, further comprising magnetic structures incorporated into or defining said dividing walls to create a magnetic field within said troughs so as to expose any substance contained within the plurality of receptacles received within said receptacle receiving troughs to said magnetic field.

22. A work station for simultaneously performing multiple assays, said work station comprising:
(a) a receptacle holding structure constructed and arranged to hold each of a plurality of receptacles in one of a plurality of receptacle sets, each set including at least two receptacles;
(b) a substance transfer device constructed and arranged to operatively interact with the plurality on the receptacles of at least two of the receptacle sets held in said receptacle holding structure to simultaneously dispense substance into each of the receptacles of a first receptacle set of the at least two receptacle sets and to simultaneously remove substance from each of the receptacles of a second receptacle set of the at least two receptacle sets, wherein said substance transfer device is constructed and arranged to simultaneously remove substance from each of the receptacles of the second receptacle set at about the same time that said substance transfer device is simultaneously dispensing substance into each of the receptacles of the first receptacle set;
(c) the receiving structure for receiving a removable contamination limiting element holding device for removably holding a plurality of contamination limiting elements which are operatively engageable by said substance transfer device to limit contact between said substance transfer device and a potentially contaminating substance dispensed or removed by said substance transfer device, said receiving structure being constructed and arranged so that the contamination limiting element holding device held thereby is positioned and oriented to:
  (i) receive and removably hold the plurality of contamination limiting elements in an operative orientation in which the contamination limiting elements can be operatively engaged by said substance transfer device, and
  (ii) allow said substance transfer device to simultaneously engage two or more of the plurality of contamination limiting elements and allow the two or more contamination limiting elements engaged by said substance transfer device to be removed from the contamination limiting element holding device; and
(d) a substance transfer device positioning mechanism including a receptacle registration structure associated with portions of said receptacle holding structure corresponding to each of said receptacle sets, a transfer registration structure fixed to said substance transfer device, and a contamination limiting element registration structure associated with and said receiving structure,
  (i) said transfer registration structure being constructed and arranged to be selectively engageable with a portion of said contamination limiting element registration structure to thereby permit said substance transfer device to be positioned with respect to a contamination limiting element holding device operatively held by said receiving structure to allow said substance transfer device to operatively engage two or more contamination limiting elements held in the contamination limiting element holding device, and
  (ii) said transfer registration structure being constructed and arranged to be selectively engageable with a portion of said receptacle registration structure to thereby position said substance transfer device with respect to any two or more of the receptacle sets held in said receptacle holding structure to permit said substance transfer device to allow said substance transfer device to:
    (1) simultaneously dispense substance into each of the receptacles of a first receptacle set of the two or more receptacle sets,
    (2) simultaneously remove substance from each of the receptacles of a second receptacle set of the two receptacle sets, or
    (3) simultaneously dispense substance into each of the receptacles of the first receptacle set and simultaneously remove substance from each of the receptacles of the second receptacle set at about the same time that said substance transfer device is simultaneously dispensing substance into each of the receptacles of the first receptacle set.

23. The work station of claim 22, further comprising a removable contamination limiting element holding device operatively held by said receiving structure.

24. A work station for simultaneously performing multiple assays, said work station comprising:
(a) a receiving structure for receiving a removable receptacle holding device for holding each of a plurality of receptacles in one of a plurality of receptacle sets;
(b) a substance transfer device constructed and arranged to operatively interact with receptacles of at least two receptacle sets held in a receptacle holding device carried by said receiving structure to simultaneously dispense substance into each of the receptacles of a first receptacle set of the at least two receptacle sets and to simultaneously remove substance from each of the receptacles of a second receptacle set of the at least two receptacle sets, wherein said substance transfer device is constructed and arranged to simultaneously remove substance from each of the receptacles of the second receptacle set at about the same time that said substance transfer device is simultaneously dispensing substance into each of the receptacles of the first receptacle set;
(c) a contamination limiting element holding structure for removably holding a plurality of contamination limiting elements which are operatively engageable by said substance transfer device to limit contact between said substance transfer device and a potentially contaminating substance dispensed or removed by said substance transfer device, said contamination limiting element holding structure being constructed and arranged to:
  (i) receive and removably hold the plurality of contamination limiting elements in an operative orientation in which the contamination limiting elements can be operatively engaged by said substance transfer device, and
  (ii) allow said substance transfer device to simultaneously engage two or more of the plurality of contamination limiting elements and allow the two or more contamination limiting elements engaged by said substance transfer device to be removed from said contamination limiting element holding structure; and
(d) a substance transfer device positioning mechanism including a receptacle registration structure associated with said receiving structure, the transfer registration structure fixed to said substance transfer device, and a contamination limiting element registration structure associated with portions of said contamination limiting element holding structure, (i) said transfer registration structure being constructed and arranged to be selectively engageable with the portion of said contamination limiting element registration structure to thereby permit said substance transfer device to be positioned with respect to said contamination limiting element holding structure to allow said substance transfer device to operatively engage the two or more contamination limiting elements, and (ii) said transfer registration structure being constructed and arranged to be selectively engageable with a portion of said receptacle registration structure to thereby position said substance transfer device with respect to any two or more of the receptacle sets held in a receptacle holding device carried by said receiving structure to permit said substance transfer device to:

(1) simultaneously dispense substance into each of the receptacles of the first receptacle set of the two or more receptacle sets, (2) simultaneously remove substance from each of the receptacles of the second receptacle set of the two or more receptacle sets, or (3) simultaneously dispense substance into each of the receptacles of the first receptacle set and simultaneously remove substance from each of the receptacles of the second receptacle set at about the same time that said substance transfer device is simultaneously dispensing substance into each of the receptacles of the first receptacle set.

25. The work station of claim 24, further comprising a removable receptacle holding device operatively held by said receiving structure.

* * * * *